US006667427B1

(12) United States Patent
Bao et al.

(10) Patent No.: US 6,667,427 B1
(45) Date of Patent: Dec. 23, 2003

(54) SCLEROTINIA-INDUCIBLE PROMOTERS AND THEIR USES

(75) Inventors: Zhangmeng Bao, Urbandale, IA (US); Jonathan P. Duvick, Des Moines, IA (US); Xu Hu, Urbandale, IA (US); Guihua Lu, Urbandale, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 158 days.

(21) Appl. No.: 09/685,292

(22) Filed: Oct. 10, 2000

Related U.S. Application Data

(60) Provisional application No. 60/159,315, filed on Oct. 14, 1999.

(51) Int. Cl.$^7$ ............................ C12N 5/09; C12N 15/29; C12N 15/82; A01H 5/00; A01H 5/10

(52) U.S. Cl. ...................... 800/287; 800/278; 800/298; 800/295; 800/320; 800/317; 800/322; 800/279; 435/320.1; 435/419; 435/468; 536/23.6; 536/24.1

(58) Field of Search ....................... 800/278, 279, 800/322, 320, 298, 287, 317, 295; 536/23.6, 24.1; 435/320.1, 419, 468

(56) References Cited

U.S. PATENT DOCUMENTS 5,801,028 A  9/1998  Bressan et al.

FOREIGN PATENT DOCUMENTS

| EP | 0332104 A2 | 9/1989 |
| EP | 0392225 A2 | 10/1990 |
| EP | 0460753 A2 | 12/1991 |
| EP | 1 033 405 A2 | 9/2000 |
| WO | WO 92/17580 A1 | 10/1992 |
| WO | WO 93/05153 A1 | 3/1993 |
| WO | WO 94/08010 A1 | 4/1994 |
| WO | WO 95/19443 A2 | 7/1995 |
| WO | WO 98/13478 A2 | 4/1998 |
| WO | WO 99/04012 A1 | 1/1999 |
| WO | WO 99/50428 A2 | 10/1999 |
| WO | WO 00/11175 A1 | 3/2000 |
| WO | WO 00/11196 A1 | 3/2000 |
| WO | WO 00/68405 A2 | 11/2000 |
| WO | WO 00/78983 A2 | 12/2000 |

OTHER PUBLICATIONS

International Search Report mailed Jun. 5, 2001 for International Application No. PCT/US00/28489 filed Oct. 13, 2000.
U.S. patent application Ser. No. 09/589,733, Bidney et al., filed, Jun. 8, 2000.
Ceccardi et al. (1998) "A Novel Protein Associated with Citrus Blight Has Sequence Similarities to Expansin," *Plant Molecular Biology* 38:775–783.
Datta et al. (1999) Database BIOSIS Accession No. PREV199903310941, "Over-Expression of the Cloned Rice Thaumatin-Like Protein (PR-5) Gene in Transgenic Rice Plants Enhances Environmental Friendly Resistance to Rhizoctonia Solani Causing Sheath Blight Disease," Abstract,*Theorectical and Applied Genetics* 98(6–7):1138–1145. (XP–002151843).
Gentzbittel et al. (1998), "Cloning of Molecular Markers for Disease Resistance in Sunflower, *Helianthus annus L.,*" *Chem. Appl. Genet.* 96:519–525.
Hu et al. (1997) "Cloning and Expression of a PR5–Like Protein from*Arabidopsis*: Inhibition of Fungal Growth by Bacterially Expressed Protein,"*Plant Molecular Biology* 34:949–959.
Jung et al. (1993) "Sunflower (*Helianthus annuus L.*) Pathogenesis–Related Proteins,"*Plant Physiol.* 101:873–880.
Jung et al. (1995) "Different Pathogenesis–Related–Proteins and Expressed in Sunflower (*Helianthus annuus L.*) in Response to Physical, Chemical and Stress Factors,"*J. Plant Physiol.* 145:153–160. (XP–000960401).
Koiwa et al. (1997) Database BIOSIS Accession No. PREV199799712464, "Purification and Characterization of Tobacco Pathogenesis–Related Protein PR–5d, an Antifungal Thaumatin–Like Protein," Abstract, *Plant and Cell Physiology* 38(7):783–791. (XP–002151842).
Liu et al. (1994) "Osmotin Overexpression in Potato Delays Development of Disease Symptoms"*Proc. Natl. Acad. Sci USA* 91:1888–1892.
Liu et al. (1995) "Fine Structure and Function of the Osmotin Gene Promoter"*Plant Molecular Biology* 29:1015–1026.
Liu et al. (1996) Database BIOSIS Accession No. PREV199799414966, "*In Vivo* and *In Vitro* Activity of Truncated Osmotin That is Secreted into the Extracellular Matrix,"*Plant Science* 121(2):123–1341. (XP–002151844).
Loulakakis (1997) "Nucleotide Sequence of a*Vitis Vinifera L.* cDNA (Accession No. Y10992) Encoding for Osmotin–Like Protein (PGR97–064),"*Plant Physiol.* 113:1464–1465. (XP–002151835).
Ronald (1998) "Resistance Gene Evolution," *Plant Biology* 1:294–298.
Sato et al. (1995) "Synthesis and Secretion of Tobacco Neutral PR–5 Protein by Transgenic Tobacco and Yeast," *Biochem. and Biophys. Res. Commun.* 211(3):909–913.

(List continued on next page.)

*Primary Examiner*—Elizabeth F. McElwain
*Assistant Examiner*—Medina A. Ibrahim
(74) *Attorney, Agent, or Firm*—Pioneer Hi-Bred International, Inc.

(57) ABSTRACT

Compositions and methods to aid in protecting plants from invading pathogenic organisms are provided. The compositions of the invention comprise anti-pathogenic nucleotide sequences, including their promoters, and polypeptides encoded by the anti-pathogenic nucleic acid sequences. The compositions find use in methods for reducing or eliminating damage to plants caused by plant pathogens. Transformed plants, plant cells, tissues, and seed are also provided having enhanced disease resistance.

12 Claims, 2 Drawing Sheets-

OTHER PUBLICATIONS

Sato et al., Database EMBL Accession No. D76437, "Nicotiana Sylvestris DNA for Neutral PR–5 (Osmotin–Like Protein, PR–5d), Complete CDs," Jun. 25, 1996. (XP–002151841).

Sato et al. (1996) Database BIOSIS Accession No. PREV199699006022, "Ethylene–Induced Gene Expression of Osmotin–like Protein, a Neutral Isoform of Tabacco PR–5, is Mediated by the AGCCGCDC cis–sequence," Abstract,*Plant and Cell Physiology* 37(3):249–255. (XP–002151840).

Thomma et al. (1998) "Separate Jasmonate–Dependent and Salicylate–Dependent Defense–Response Pathways in *Arabidopsis* are Essential for Resistance to Distinct Microbial Pathogens"*Proc. Natl. Acad. Sci. USA* 95:15107–15111.

Vigers et al. (1992) "Thaumatin–Like Pathogenesis–Related Proteins areAntifungal" *Plant Science* 83:155–161. (XP–000960338).

Yamakawa et al. (1998) "Spermine is a Salicylate–Independent Endogrnous Inducer for Both Tobacco Acidic Pathogenesis–Related Proteins and Resistance against Tobacco Mosaic Virus Infection"*Plant Physiol.* 118:1213–1222.

Zhou et al. (1997) "The Pto Kinase Conferring Resistance to Tomato Bacterial Speck Disease Interacts with Proteins that Bind acis–element of Pathogenesis–Related Genes"*The EMBO Journal* 16(11):3207–3215.

Zhu et al. (1995) "Activation of Two Osmotion–like Protein Genes by Abiotic Stimuli and Fungal Pathogen in Transgenic Potato Plants,"*Plant Physiol.* 108:929–937. (XP–002151838).

NCBI Database Accession No. X12739.
NCBI Database Accession No. X15224.
NCBI Database Accession No. X15223.
NCBI Database Accession No. AAD03398.
NCBI Database Accession No. U03860.
NCBI Database Accession No. U30472.
NCBI Database Accession No. AC001229.

Dittrich, et al., "Molecular Cloning, Expression, and Induction of Berberine Bridge Enzyme, an Enzyme Essential to the Formation of Benzophenanthridine Alkaloids in the Response of Plants to Pathogenic Attack," *Proc. Natl. Acad. Sci.*, 1991, pp. 9969–9973, vol. 88.

Domon, et al., "Nucleotide Sequence of Two Anther–Specific cDNAs from Sunflower (*Helianthus annus L.*), " *Plant Molecular Biology*, 1990, pp. 643–646, vol. 15, Nijoff Publishers, NL.

Domon, C., et al., "Exon Shufffling in Anther–Specific Genes from Sunflower," *Molecular & General Genetics*, 1994, pp. 312–317, vol. 244(2). (EMBL Accession No. X77993).

Facchini, et al., "Molecular Characterization of Berberine Bridge Enzyme Genes from Opium Poppy," *Plant Physiology*, 1996, pp. 1669–1677, vol. 112.

Hauschild, et al., "Isolation and Analysis of a Gene *bbe1* Encoding the Berberine Bridge Enzyme from the California Poppy *Eschscolzia californica*," *Plant Molecular Biology*, 1998, pp. 473–478, vol. 36, Nijhoff Publishers, NL.

Regente, M., et al., "A Sunflower Leaf Antifungal Peptide Active against *Sclerotinia sclerotiorum*, " *Physiologia Pantarum*, 1997, pp. 178–182, vol. 100(1).

Urdangarín, M., et al., "A Defensin Gene Expressed in Sunflower Inflorescene," *Plant Physiology and Biochemistry*, 2000, pp. 253–258, vol. 38(3).

EMBL Database Report for Accession No. AC007060, Mar. 15, 1999 (XP002160554).

```
AAATTTGGTCAACACCTTATTTTGTAAAAGAGGTACAAAAACAAAGATTT
TTTCAAAATTCCAAATCACCCTATCATGTAAGTGCATTGATGTAAAAGTG
GAAATGATATTATTCATATGGTCCTGTTGTGCTTTTGTTTTCCTCTAATA
TGAGTTCATGATCTAATCCGGTGATTTGAAGACATTGATGTTGAATCGAA
TGAGATGGTTGATGTAATGTGGTCGTATTACAAACAAATAGTAATTAAGT
AATCTAAATAACTTTCCCGAGCCCGGGAAGCAATCCCGGGTAAAACCTA
GTTTTATATTAACGAATTGTATCGTATATTAAATTTTATTTTTTATAATA
TAATATTTATCGCACTTCGCTTTTGATCTCCCTATCTCCATACATGACA
TGTTTTTAATTTCTCAAATCAAATTGATAAATTAAGCCAATAATAACTCC
AGCTTGTAAAATAATAATTACCAAACTTAAGTTCATTTCTATTTAGTAAA
           MRE-like
ATATGTCATAACAATTATTAAATCTCGACAAAACAATATAATGATCACAA
TGGACATTGTGAGAAACTAGATTGCTATATAATATGTGATATTTAAGCC
                                ZAP-like
TTTAATCATATTAGAGATAGCAAACTCTACATTTTAGACCGATCAGTT
AGCAGGCATCGATGCATTGTGAGTTAAGCTAGGTTAGGCGGGTTTAATCG
TTGAACATTAACACGGCCAATATAGTTATTTATGTAACAACATTAACTCT
AATCCAGACACACTTAGTAATCATATAACCCGAACACGAGCCATTTAACT
CATTTATCTAAACAAAGTCAAATGGTGTGACACGTTGGTTGGTTGTGTACA
AGTTGTTTACGGGTTGGAGGGTTAGACTGGTCGTAATTCGTAAAGGGGTT
TACGAGTCGGTATGTTTAATTAAATGGATTAAACATGTCAATCAGATTAC
AACCCACATAACTAAACGAGTAAAATGGTCGATCCGTCACAACCTGTTTA
TTAAATGGGTTAGACATGACAATCCAAAACTTGATTATTATCGTATCATA
          MRE-like
CTATCATATTCGTGTTGTGTTTCATGTCTTGTCAAAATTATCATCCTTA
ATTATTAATCGGTCATTTTATAATTTGTACACAGTTAATATATCAAAC
ATGCCATAAAAGTTTATTCCAAAAAAAAATGTATTAATCTATCATATAT
TCATATGTATTATAATTTTTTACTCATGTTAAGACTATTCTTTCAATCT
TATCAAAATTAGTTCACTATCAACTCACACTTCTAAGTCTTGGGAATTTT
CTTTGTACCATTGTTAAAATTCCAGCCTAACTTTTGGACATATGTTATAC
CAAT-box                                TATA-box
AATCTTTGAAAAGTTTGTATGCAACCCCTCTCTATTCCCTAATATATACC
CGTTTAATAAAAATCATCTTCAACCCACACTACTTGACATACAAACATG
```

Figure 1

```
ATCACAAAAACAGACGATATACACATGTATACATCACATTAAAAACAAGG
TAAAATCCGAATACACATAGAATACACATGTGTACATCGCAGTTAAACAA
AGCAAGAATAATGAATTTAAAATAGGAAAGATATTATGGATAAGGAATTA
AAATGGGAAATATGTAACTGATTTTAATTATTAAGATAATGATTTAAATC
TATTTTTTATAAAATTAGTTTCATATTTAATTTATGAGAGAGAACATGAT
TTATGCAACAATTTAAGATAAAAATTACACATATACCCTTTTTGTATTTA
ATTAAATGAAAAAATTTACCATATAATTACCATCATGCCACTCATCTAA
ATCTCAAGATTATATAAATCAAAGGCCAAGATGAGTTCACACAGTTCACA
ACTTAGGGGGGTGTTCACTCTTGAACCTAATCCTCTATATATATATAT
ATAGAGAGAGAGAGAGGGAGAGAGAGGGAGGGAGAGAGACTAGTTATT
GTACAAATTGTCTTAACGTACGATGCGTACGAGATGCTGCGAATAATGGT
            MRE-like
TCATAACATGCGAGTTTTGTTTTTTTGAACATGCGATTTTTTTACAAT
ATACGATTTTTTAATAACATGCGACGTTTTTGTTTTTTGTTTTTTTTG
AACATGCCACCTTTGGTTTTAAAACCTTATGCAACCATTTTGCGGTTTT
TAAAATATTATATTGGTTTGAAAATATACGAGTAAACTTGTGTGTGTTTT
TAAAGGAAAGATCTTAAACATAACTAAGAAGTGTATTTGTTATCCACGAT
                                              W-box
CTAGAATCTAGAGATTAAACTACATGTCCCACTTCCTTGACTTATTGATA
                    W-box MRE-like
AATCATTTGTATTTTGTTGACTACCTACAACGAAAATGTTGCACGGTTTT
    TATA box
CAGTTATAAAAGGATAGCACTTTGGTTCTCATCATGACCAAAGTAATTAA
                                                Met
AAGACTTCACAGATCAAATCTAAGGGTTCCAAAAAACACATTCAAAAATG
GGTTTGATGACTAGAGCTGTTATCTTGATCGCTATGGTTGCATGTCTCAC
ATCGGTTGCTCATGCCATTGCTGGCCAAGCAACCTTCTACACTCCTCCCT
        First intron
ACGTTCGTAAGTATATCGACATATATTAAACACTTCACCAGAGTTTATTT
TTCTTAATTTGTGTAGCTTGTTTTGAGTTTTATCGTGGTATATATGTAG
CATCGTCTTGTTTTGGCTTCGAAGACCGCGGTGTTATGATTCTAGCAGCA
AACAGCGGTTTGTTTAACAACAGAGCCGCGTGTGGAACTAG
```

Figure 2

SEQUENCE LISTING

```
<160> NUMBER OF SEQ ID NOS: 22

<210> SEQ ID NO 1
<211> LENGTH: 910
<212> TYPE: DNA
<213> ORGANISM: Helianthus annuus
<220> FEATURE:
<221> NAME/KEY: CDS
<222> LOCATION: (8)...(695)

<400> SEQUENCE: 1 tacaaac atg act tgt gcc aaa aac ctt cta ctc tcg atc acc ctt ctt       49
        Met Thr Cys Ala Lys Asn Leu Leu Leu Ser Ile Thr Leu Leu
        1               5                   10 tcc atc ggt tgc ttc act ctc act cga gga gcc act ttc gat gtc ata       97
Ser Ile Gly Cys Phe Thr Leu Thr Arg Gly Ala Thr Phe Asp Val Ile
15                  20                  25                  30 aac caa tgt caa tac cct gtt tgg gcc gct tgg gcc tct acc acg cct      145
Asn Gln Cys Gln Tyr Pro Val Trp Ala Ala Trp Ala Ser Thr Thr Pro
                35                  40                  45 ggt gga ggc aag cgg ctt gaa aat ggt caa tct tgg caa atc aca gtt      193
Gly Gly Gly Lys Arg Leu Glu Asn Gly Gln Ser Trp Gln Ile Thr Val
            50                  55                  60 gca ccc ggg act gct caa gct cgt att tgg gga aga act ggt tgc aac      241
Ala Pro Gly Thr Ala Gln Ala Arg Ile Trp Gly Arg Thr Gly Cys Asn
65                  70                  75 ttt gat gcc aat gga aga ggg agg tgt gac acc ggt gat tgc aat gga      289
Phe Asp Ala Asn Gly Arg Gly Arg Cys Asp Thr Gly Asp Cys Asn Gly
    80                  85                  90 atg ctc gaa tgt caa ggt tat ggg gcg cca ccc aac act tta gct gaa      337
Met Leu Glu Cys Gln Gly Tyr Gly Ala Pro Pro Asn Thr Leu Ala Glu
```

```
                95                  100                 105                 110
ttc gcg ctt aat caa gac aac aat aat gac ttt gtt gac ata tct ctt          385
Phe Ala Leu Asn Gln Asp Asn Asn Asn Asp Phe Val Asp Ile Ser Leu
            115                 120                 125 gtt gat ggg ttt aat atc cct atg gag ttt agc ccg gtt ggg gct tcg          433
Val Asp Gly Phe Asn Ile Pro Met Glu Phe Ser Pro Val Gly Ala Ser
            130                 135                 140 tgc aag aca atg agg tgt gcg ggt aat cta aat ggc gag tgc cct aat          481
Cys Lys Thr Met Arg Cys Ala Gly Asn Leu Asn Gly Glu Cys Pro Asn
            145                 150                 155 gaa cta cga aca caa gga gga tgc aac aat cct tgc acg gtt tac aaa          529
Glu Leu Arg Thr Gln Gly Gly Cys Asn Asn Pro Cys Thr Val Tyr Lys
    160                 165                 170 act aac gag tat tgt tgc acc aat ggg ccg ggt agt tgt gga cca act          577
Thr Asn Glu Tyr Cys Cys Thr Asn Gly Pro Gly Ser Cys Gly Pro Thr
175                 180                 185                 190 ccg ttg tct agg ttc ttt aaa gac agg tgt cct gat gct tat agt tac          625
Pro Leu Ser Arg Phe Phe Lys Asp Arg Cys Pro Asp Ala Tyr Ser Tyr
            195                 200                 205 cct caa gat gac ccg acc agt cta ttt act tgc ccg ggt ggt act aac          673
Pro Gln Asp Asp Pro Thr Ser Leu Phe Thr Cys Pro Gly Gly Thr Asn
            210                 215                 220 tac aaa gtt gtg ttc tgt cca t aaactctata tgagagttgt aaactagtaa          725
Tyr Lys Val Val Phe Cys Pro
            225 tgataaaata agagttccac ctcatagagt gtggcttctc tagtctcgtc aacaaaataa       785 ggggacttat gcccatccat atatcttcaa actttgtttg attgttgtac ttgtacgtgt       845 tacaaagatt tatttatata ataaaaaagt aatattgtct attttataaa aaaaaaaaa       905 aaaaa                                                                   910
```

<210> SEQ ID NO 2
<211> LENGTH: 229
<212> TYPE: PRT
<213> ORGANISM: Helianthus annuus

<400> SEQUENCE: 2

```
Met Thr Cys Ala Lys Asn Leu Leu Leu Ser Ile Thr Leu Leu Ser Ile
  1               5                   10                  15

Gly Cys Phe Thr Leu Thr Arg Gly Ala Thr Phe Asp Val Ile Asn Gln
                 20                  25                  30

Cys Gln Tyr Pro Val Trp Ala Ala Trp Ala Ser Thr Thr Pro Gly Gly
             35                  40                  45

Gly Lys Arg Leu Glu Asn Gly Gln Ser Trp Gln Ile Thr Val Ala Pro
         50                  55                  60

Gly Thr Ala Gln Ala Arg Ile Trp Gly Arg Thr Gly Cys Asn Phe Asp
 65                  70                  75                  80

Ala Asn Gly Arg Gly Arg Cys Asp Thr Gly Asp Cys Asn Gly Met Leu
                 85                  90                  95

Glu Cys Gln Gly Tyr Gly Ala Pro Pro Asn Thr Leu Ala Glu Phe Ala
            100                 105                 110

Leu Asn Gln Asp Asn Asn Asn Asp Phe Val Asp Ile Ser Leu Val Asp
            115                 120                 125

Gly Phe Asn Ile Pro Met Glu Phe Ser Pro Val Gly Ala Ser Cys Lys
        130                 135                 140

Thr Met Arg Cys Ala Gly Asn Leu Asn Gly Glu Cys Pro Asn Glu Leu
145                 150                 155                 160
```

```
Arg Thr Gln Gly Gly Cys Asn Asn Pro Cys Thr Val Tyr Lys Thr Asn
            165                 170                 175

Glu Tyr Cys Cys Thr Asn Gly Pro Gly Ser Cys Gly Pro Thr Pro Leu
        180                 185                 190

Ser Arg Phe Phe Lys Asp Arg Cys Pro Asp Ala Tyr Ser Tyr Pro Gln
        195                 200                 205

Asp Asp Pro Thr Ser Leu Phe Thr Cys Pro Gly Gly Thr Asn Tyr Lys
    210                 215                 220

Val Val Phe Cys Pro
225

<210> SEQ ID NO 3
<211> LENGTH: 622
<212> TYPE: DNA
<213> ORGANISM: Helianthus annuus
<220> FEATURE:
<221> NAME/KEY: CDS
<222> LOCATION: (41)...(431)

<400> SEQUENCE: 3
cacagatcaa atctaagggt tccaaaaaac acattcaaaa atg ggt ttg atg act        55
                                             Met Gly Leu Met Thr
                                              1               5 aga gct gtt atc ttg atc gct atg gtt gca tgt ctc aca tcg gtt gct      103
Arg Ala Val Ile Leu Ile Ala Met Val Ala Cys Leu Thr Ser Val Ala
             10                  15                  20 cat gcc att gct ggc caa gca acc ttc tac act cct ccc tac gtt cca      151
His Ala Ile Ala Gly Gln Ala Thr Phe Tyr Thr Pro Pro Tyr Val Pro
         25                  30                  35 tcg tct tgt ttt ggc ttc gaa gac cgc ggt gtt atg att cta gca gca      199
Ser Ser Cys Phe Gly Phe Glu Asp Arg Gly Val Met Ile Leu Ala Ala
     40                  45                  50 aac agc ggt ttg ttt aac aac aga gcc gcg tgt gga act agg tac cgt      247
Asn Ser Gly Leu Phe Asn Asn Arg Ala Ala Cys Gly Thr Arg Tyr Arg
 55                  60                  65 gta act tgc acc agt gga acc aac gga ggt gtt cca caa cct tgc act      295
Val Thr Cys Thr Ser Gly Thr Asn Gly Gly Val Pro Gln Pro Cys Thr
 70                  75                  80                  85 ggc agg agc gtt gat gtt aca gtt gtt gat ctt tgt ccc gga tgt gct      343
Gly Arg Ser Val Asp Val Thr Val Val Asp Leu Cys Pro Gly Cys Ala
                 90                  95                 100 tca gat caa gtt gat ctt tcc caa gag gca ttc gca gtg att gcc aat      391
Ser Asp Gln Val Asp Leu Ser Gln Glu Ala Phe Ala Val Ile Ala Asn
            105                 110                 115 act gat gca ggg aga att aac att gac tat aac agg atc t aagtaataaa     441
Thr Asp Ala Gly Arg Ile Asn Ile Asp Tyr Asn Arg Ile
        120                 125                 130 acatgcatgc aagatgccaa taataaactc ttttatgagt attcttcaga ataacaaga     501 ctacagggcg ttgtaaccat atttgttacg tgaataaaat gttactttct gtgcgaattt    561
gaaacattgt tacgtgaata aaacgttttc tatccattaa aaaaaaaaaa aaaaaaaaa     621 a                                                                    622

<210> SEQ ID NO 4
<211> LENGTH: 130
<212> TYPE: PRT
<213> ORGANISM: Helianthus annuus

<400> SEQUENCE: 4
```

```
Met Gly Leu Met Thr Arg Ala Val Ile Leu Ile Ala Met Val Ala Cys
 1               5                  10                  15

Leu Thr Ser Val Ala His Ala Ile Ala Gly Gln Ala Thr Phe Tyr Thr
                 20                  25                  30

Pro Pro Tyr Val Pro Ser Ser Cys Phe Gly Phe Glu Asp Arg Gly Val
             35                  40                  45

Met Ile Leu Ala Ala Asn Ser Gly Leu Phe Asn Asn Arg Ala Ala Cys
 50                  55                  60

Gly Thr Arg Tyr Arg Val Thr Cys Thr Ser Gly Thr Asn Gly Gly Val
 65                  70                  75                  80

Pro Gln Pro Cys Thr Gly Arg Ser Val Asp Val Thr Val Val Asp Leu
                 85                  90                  95

Cys Pro Gly Cys Ala Ser Asp Gln Val Asp Leu Ser Gln Glu Ala Phe
            100                 105                 110

Ala Val Ile Ala Asn Thr Asp Ala Gly Arg Ile Asn Ile Asp Tyr Asn
            115                 120                 125

Arg Ile
    130

<210> SEQ ID NO 5
<211> LENGTH: 1448
<212> TYPE: DNA
<213> ORGANISM: Helianthus annuus

<400> SEQUENCE: 5
aaatttggtc aacaccttat tttgtaaaag aggtacaaaa acaagatttt tttcaaaatt     60
ccaaatcacc ctatcatgta agtgcattga tgtaaaagtg gaaatgatat tattcatatg    120
gtcctgttgt gcttttgttt tcctctaata tgagttcatg atctaatccg gtgatttgaa    180
gacattgatg ttgaatcgaa tgagatggtt gatgtaatgt ggtcgtatta caaacaaata    240
gtaattaagt aatctaaata actttcccga gcccgggaag caatcccggg taaaaaccta    300
gttttatatt aacgaattgt atcgtatatt aaattttatt ttttataata taatattttat    360 cgcacttcgc ttttgatctc ccctatctcc atacatgaca tgttttttaat ttctcaaatc    420 aaattgataa attaagccaa taataactcc agcttgtaaa ataataatta ccaaacttaa    480
gttcatttct atttagtaaa atatgtcata acaattatta aatctcgaca aaacaatata    540
atgatcacaa tggacattgt gagaaaacta gattgctata taatatgtga tatttaagcc    600
tttaatcata ttagagatag caaactctac attttagacc gatcagttag caggcatcga    660
tgcattgtga gttaagctag gttaggcggg tttaatcgtt gaacattaac acggccaata    720
tagttattta tgtaacaaca ttaactctaa tccagacaca cttagtaatc atataacccg    780
aacacgagcc atttaactca tttatctaaa caaagtcaaa tggtgtgaca cgttggttgg    840
ttgtgtacaa gttgtttacg ggttggaggg ttagactggt cgtaattcgt aaagggggttt    900 acgagtcggt atgtttaatt aaatggatta acatgtcaa tcagattaca acccacataa    960
ctaaacgagt aaaatggtcg atccgtcaca acctgtttat taaatgggtt agacatgaca   1020
atccaaaact tgattattat cgtatcatac tatcatattc gtgttgtgtt tcatgtcttg   1080
tcaaaaatta tcatccttaa ttattaatcg gtcattttta taatttttgta cacagttaat   1140 atatcaaaca tgccataaaa agtttattcc aaaaaaaaat gtattaatct atcatatatt   1200
catatgtatt ataatttttt tactcatgtt aagactattc tttcaatctt atcaaaatta   1260
gttcactatc aactcacact tctaagtctt gggaattttc tttgtaccat tgttaaaatt   1320
```

```
ccagcctaac ttttggacat atgttataca atctttgaaa agtttgtatg caacccctct   1380
ctattcccta atatataccc gtttaataaa aatcatcttc aacccacact acttgacata   1440
caaacatg                                                            1448
```

<210> SEQ ID NO 6
<211> LENGTH: 1291
<212> TYPE: DNA
<213> ORGANISM: Helianthus annuus

<400> SEQUENCE: 6

```
atcacaaaaa cagacgatat acacatgtat acatcacatt aaaaacaagg taaaatccga     60
atacacatag aatacacatg tgtacatcgc agttaaacaa agcaagaata atgaatttaa    120
aataggaaag atattatgga taaggaatta aaatgggaaa tatgtaactg attttaatta    180
ttaagataat gatttaaatc tattttttat aaaattagtt tcatatttaa tttatgagag    240
agaacatgat ttatgcaaca atttaagata aaaattacac atatacccctt tttgtattta    300 ataacatgat ttatgcaaca atttaagata aaaattacac atatacccctt tttgtattta    360 attaaatgaa aaaatttac catataatta ccatcatgcc actcatctaa atctcaagat    420
ttgaacctaa tcctctatat atatatatat atagagagag agagagaggg agagagaggg    480
agggagagag actagttatt gtacaaattg tcttaacgta cgatgcgtac gagatgctgc    540
gaataatggt tcataacatg cgagttttgt tttttttgaa catgcgattt tttttacaat    600
atacgatttt ttaataacat gcgacgtttt ttgtttttg ttttttttg aacatgccac    660 ctttggtttt taaaaccta tgcaaccatt ttgcggtttt taaatatta tattggtttg    720 aaaatatacg agtaaacttg tgtgtgtttt taaaggaaag atcttaaaca taactaagaa    780
gtgtatttgt tatccacgat ctagaatcta gagattaaac tacatgtccc acttccttga    840
cttattgata aatcatttgt attttgttga ctacctacaa cgaaaatgtt gcacggtttt    900
cagttataaa aggatagcac tttggttctc atcatgacca aagtaattaa aagacttcac    960
agatcaaatc taagggttcc aaaaaacaca ttcaaaaatg ggtttgatga ctagagctgt   1020
tatcttgatc gctatggttg catgtctcac atcggttgct catgccattg ctggccaagc   1080
aaccttctac actcctccct acgttcgtaa gtatatcgac atatattaaa cacttcacca   1140
gagtttattt ttcttaattt gtgtagcttg ttttgagttt ttatcgtggt atatatgtag   1200
catcgtcttg ttttggcttc gaagaccgcg gtgttatgat tctagcagca aacagcggtt   1260
tgtttaacaa cagagccgcg tgtggaacta g                                  1291
```

<210> SEQ ID NO 7
<211> LENGTH: 10
<212> TYPE: DNA
<213> ORGANISM: Artificial Sequence
<220> FEATURE:
<223> OTHER INFORMATION: oligonucleotide primer

<400> SEQUENCE: 7

```
ggtactccac                                                            10
```

<210> SEQ ID NO 8
<211> LENGTH: 10
<212> TYPE: DNA
<213> ORGANISM: Artificial Sequence
<220> FEATURE:
<223> OTHER INFORMATION: oligonucleotide primer -continued

```
<400> SEQUENCE: 8
gaccgcttgt                                                    10

<210> SEQ ID NO 9
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 9
ccatgatggc aatggaagag                                         20

<210> SEQ ID NO 10
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 10
gcgattaagt tgggtaacgc cagggt                                  26

<210> SEQ ID NO 11
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 11
tccggctcgt atgttgtgtg gaattg                                  26

<210> SEQ ID NO 12
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 12
agattacccg cacacctcat tgtcttgc                                28

<210> SEQ ID NO 13
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 13
tacaaacatg acttgtgcca aaaccttc                                29

<210> SEQ ID NO 14
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 14
gcgattaagt tgggtaacgc cagggt                                  26

<210> SEQ ID NO 15
<211> LENGTH: 24
```

```
<212> TYPE: DNA
<213> ORGANISM: Artificial Sequence
<220> FEATURE:
<223> OTHER INFORMATION: oligonucleotide primer

<400> SEQUENCE: 15
tggttacaac gccctgtagt cttg                                           24

<210> SEQ ID NO 16
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 16
gcgattaagt tgggtaacgc cagggt                                         26

<210> SEQ ID NO 17
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 17
gtgccgcaca gatcaaatct aagggttc                                       28

<210> SEQ ID NO 18
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 18
gcgattaagt tgggtaacgc cagggt                                         26

<210> SEQ ID NO 19
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 19
gtaatacgac tcactatagg gc                                             22

<210> SEQ ID NO 20
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 20
actatagggc acgcgtggt                                                 19

<210> SEQ ID NO 21
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 21
```

-continued

```
agattacccg cacacctcat tgtcttgc                                              28

<210> SEQ ID NO 22
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 22
ctagttccac acgcggctct gttgtta                                               27
```

SCLEROTINIA-INDUCIBLE PROMOTERS AND THEIR USES

CROSS REFERENCE TO RELATED APPLICATIONS

This application claims the benefit of U.S. Provisional Application No. 60/159,315, filed Oct. 14, 1999, herein incorporated by reference.

FIELD OF THE INVENTION

The invention relates to nucleotide sequences and proteins for anti-pathogenic agents and their uses, particularly the genetic manipulation of plants with genes and promoters that enhance disease resistance.

BACKGROUND OF THE INVENTION

Among the causal agents of infectious diseases of crop plants, phytopathogenic fungi play the dominant role, not only by causing devastating epidemics, but also through the less spectacular although persistent and significant annual crop yield losses that have made fungal pathogens a serious economic factor. All flowering plant species are attacked by pathogenic fungi. To colonize plants, fungal microorganisms have evolved strategies to invade plant tissue, to optimize growth in the plant, and to propagate. Bacteria and viruses, as well as some opportunistic fungal parasites, often depend on natural openings or wounds for invasion. In contrast, many true phytopathogenic fungi have evolved mechanisms to actively traverse the plants outer structural barriers, the cuticle and the epidermal cell wall. To gain entrance, fungi generally secrete a cocktail of hydrolytic enzymes.

Despite the large number of microorganisms capable of causing disease, most plants are resistant to any given pathogen. The defense mechanisms utilized by plants can take many different forms, ranging from passive mechanical or preformed chemical barriers, which provide non-specific protection against a wide range of organisms, to more active host-specific responses that provide host- or varietal-specific resistance.

A hypersensitive response (HR) that is elaborated in response to invasion by all classes of pathogens is the most common feature associated with active host resistance. In most cases, activation of the HR leads to the death of cells at the infection site, which results in the restriction of the pathogen to small areas immediately surrounding the initially infected cells. At the whole-plant level, the HR is manifested as small necrotic lesions. The number of cells affected by the HR is only a small fraction of the total in the plant, so this response obviously contributes to the survival of plants undergoing pathogen attack.

In plants, robust defense responses to invading phytopathogens often conform to a gene-for-gene relationship. Resistance to a pathogen is only observed when the pathogen carries a specific avirulence (avr) gene and the plant carries a corresponding resistance (R) gene. Because avr-R gene-for-gene relationships are observed in many plant-pathogen systems and are accompanied by a characteristic set of defense responses, a common molecular mechanism underlying avr-R gene-mediated resistance has been postulated. Thus, disease resistance results from the expression of a resistance gene in the plant and a corresponding avirulence gene in the pathogen and is often associated with the rapid, localized cell death characteristic of the hypersensitive response. R genes that respond to specific bacteria, fungal, or viral pathogens have been isolated from a variety of plant species and several appear to encode cytoplasmic proteins.

The development of new strategies to control diseases is the primary purpose of research on plant-pathogen interactions. These include, for example, the identification of essential pathogen virulence factors and the development of means to block them, or the transfer of resistance genes into crop plants from unrelated species. An additional benefit is a better understanding of the physiology of the healthy plant through a study of the metabolic disturbances caused by plant pathogens.

SUMMARY OF THE INVENTION

Anti-pathogenic compositions and methods for their use are provided. The compositions comprise anti-pathogenic polypeptides, the nucleotide sequences encoding these polypeptides and the nucleotide sequences comprising the regulatory regions of these sequences. Particularly, sunflower pathogenesis-related protein 5-2 (PR5-2) and blight associated protein (BAP), as well as fragments and variants thereof, are provided.

The compositions are useful in protecting plants from invading pathogenic organisms. One method involves stably transforming a plant with nucleotide sequences of the invention to engineer broad-spectrum disease resistance in the plant. The nucleotide sequences are expressed from a promoter capable of driving expression in a plant cell. A second method involves controlling plant pathogens by applying an effective amount of an anti-pathogenic protein or composition to the plant environment. Additionally, the nucleotide sequences of the invention are useful as genetic markers in disease-resistance breeding programs.

Promoters of the genes of the invention find use as defense-inducible promoters. Such promoters may be used to express other coding regions, particularly other anti-pathogenic genes, including disease and insect resistance genes.

The compositions of the invention additionally find use in agricultural and pharmaceutical compositions as antifungal and antimicrobial agents. For agricultural purposes, the compositions may be used in sprays for control of plant disease. As pharmaceutical compositions, the agents are useful as antibacterial and antimicrobial treatments.

Thus, the methods of the invention find use in controlling pests, including fungal pathogens, viruses, nematodes, insects, and the like. Transformed plants, plant cells, plant tissues, and seeds, as well as methods for making such transformed compositions are additionally provided.

BRIEF DESCRIPTION OF THE DRAWINGS

FIG. 1 sets forth the nucleotide sequence of the promoter for the sunflower PR5-2 gene (set forth in SEQ ID NO:5). Putative TATA-box, CAAT box, ZAP-like, and MRE-like elements are indicated.

FIG. 2 sets forth the nucleotide sequence of the promoter for the sunflower BAP gene (set forth in SEQ ID NO:6). Putative TATA-box, CAAT box, W-Box, and MRE-like element are indicated. The first intron is underlined.

DETAILED DESCRIPTION OF THE INVENTION

A number of terms used herein are defined and clarified in the following section.

Definitions

By "agronomic trait" is intended a phenotypic trait of an agricultural plant that contributes to the performance or economic value of the plant. Such traits include disease resistance, insect resistance, nematode resistance, virus resistance, drought tolerance, high salinity tolerance, yield, plant height, days to maturity, seed nitrogen content, seed oil content, seed or fruit color, seed or fruit size, and the like.

By "anti-pathogenic compositions" is intended that the compositions of the invention have anti-pathogenic activity and thus are capable of suppressing, controlling, and/or killing the invading pathogenic organism. Such anti-pathogenic compositions of the invention include isolated sunflower PR5-2 and blight associated protein (BAP) amino acid sequences; the nucleic acid sequences encoding them; the nucleotide sequences comprising their respective promoter regions; as well as nucleotide and amino acid sequence fragments and variants thereof that retain their biological or regulatory function. The compositions find use in protecting plants against fungal pathogens, viruses, nematodes, insects, and the like by way of enhancing plant disease resistance. Additionally, the compositions can be used in formulations for their antibacterial and antimicrobial activities.

By "disease resistance" is intended that the plants avoid the disease symptoms that are the outcome various abiotic and/or biotic stresses. That is, the plant diseases and/or the associated disease symptoms caused by the various stimuli are minimized or lessened. As such, a polypeptide or a nucleic acid sequence that enhances disease resistance minimizes the physiological consequences of biotic and/or abiotic stresses which lead to plant disease. Of particular interest is minimizing or lessening the plant disease and the associated disease symptoms resulting from a response to an external stimulus, such as a pathogens, wounding, or environmental stresses, including but not limited to, drought, temperature, and salinity. The methods of the invention can be utilized to protect plants from disease, particularly those diseases that are caused by plant pathogens.

By "pathogenic agent" or "pathogen" is intended any organism that has the potential to negatively impact a plant, typically, but not exclusively, by causing disease or inflicting physical damage. Such organisms include, but are not limited to, fungi, bacteria, nematodes, mycoplasmas, viruses, and insects.

By "promoter" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate.

By "defense-inducible" is intended that transcription of a nucleotide sequence operably linked to the defense-inducible promoter is regulated when the plant is exposed to biotic and abiotic stress. By "regulate" is intended the repression or activation of transcription from a promoter region. The regulation of transcription by the promoter sequences of the present invention is defined herein as "inducible." By "inducible" is intended the ability of the promoter sequence to regulate expression of an operably linked nucleotide sequence in response to a stimulus.

By "stimulus" is intended an elemental or molecular species which either directly or indirectly regulates the activity (i.e., an increase in initiation or expression) of an inducible promoter.

By "direct action" is intended that the stimulus regulates transcription via a direct interaction between the stimulus and the DNA sequence. By "indirect action" is meant that the regulation occurs via an interaction between the stimulus and some other endogenous or exogenous component in the system, the ultimate result of the indirect action being regulation of the inducible promoter. The stimulus can result from a biotic or abiotic stress, including for example, tissue wounding (i.e., insect herbivory, wind, intentional abiotic infliction of tissue injury or wounding for the purpose of experimentation and/or expression analysis); wound-responsive chemicals (i.e., chemicals that result in the activation of wound-response signal transduction pathways, including, various hormones, jasmonic acid, abscissic acid, linolenic acid, ethylene, their chemical analogues, derivatives, precursors, and the like); pathogens (i.e, fungi, bacteria, nematodes, mycoplasmas, viruses, and insects and the like); and various environmental stresses (i.e., heat, drought, cold, reactive oxygen species and/or radiation). Hence, the promoter of the present invention can be used in combination with a nucleotide sequence that enhances disease resistance, and the compositions therefor find use in the defense of a plant against disease, pathogens, and the like.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein-encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

By "nucleic acid molecule" is intended a molecule composed of nucleotides covalently bound to one another. Nucleotides include both ribonucleotides and deoxyribonucleotides. "Nucleic acid molecule" encompasses single-stranded and double stranded forms of both DNA and RNA. Nucleic acid molecules may be naturally occurring, synthetic, or a combination of both. The linear arrangement of nucleotides in a nucleic acid molecule is referred to as a "nucleotide sequence" and, unless specified otherwise, is presented herein from left to right corresponding to the 5'-to-3' direction.

By "antisense DNA nucleotide sequence" is intended a sequence that is complementary to at least a portion of the messenger RNA (mRNA) for a targeted gene sequence.

By "foreign" is intended that the transcriptional initiation region is not found in the native plant into which the transcriptional initiation region is introduced.

A "chimeric gene" comprises a coding sequence operably linked to a transcription initiation region that is heterogolous to the coding sequence. As used herein, "heterologous" in reference to a nucleic acid is a nucleic acid that originates from a foreign species, or, if from the same species, is substantially modified from its native form in composition by deliberate human intervention. For example, a promoter operably linked to a heterologous nucleotide sequence is from a species different from that from which the nucleotide sequence was derived. If the nucleic acid sequence is from the same species, the promoter or the nucleotide sequence are substantially modified from their original form.

By "fragment" is intended a portion of the nucleotide sequence or a portion of the amino acid sequence, and hence protein encoded thereby. Fragments of a nucleotide sequence may encode protein fragments that retain the anti-pathogenic biological activity of the native protein, and hence provide disease resistance. Alternatively, fragments of a nucleotide sequence that are useful as hybridization probes, such as described elsewhere herein, generally do not encode protein fragments that retain this biological activity. Fragments of a regulatory sequence, i.e., promoter, disclosed herein may retain their promoter activity.

By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions in the same reading frame.

By "stably transformed" is intended that the nucleotide sequences introduced into a cell and/or plant using transformation methods described herein are stably incorporated into the genome of the cell and/or plant. Stably incorporated nucleotide sequences are heritable.

By "variants" is intended substantially similar sequences. For nucleotide sequences, conservative variants include those sequences that, because of the degeneracy of the genetic code, encode the amino acid sequence of one of the anti-pathogenic proteins (PR5-2 or BAP) of the invention. Naturally-occurring allelic variants such as these can be identified with the use of well-known molecular biology techniques, as, for example, with polymerase chain reaction (PCR) and hybridization techniques as outlined below. Variant nucleotide sequences also include synthetically-derived nucleotide sequences, such as those generated, for example, by using site-directed mutagenesis or DNA shuffling as described elsewhere herein, but which still encode an anti-pathogenic protein of the invention, or, in the case of variants of a promoter sequence, retain promoter activity. Generally, variants of a particular nucleotide sequence of the invention will have at least 40%, 50%, 60%, 70%, generally at least 75%, 80%, 85%, preferably about 90% to 95% or more, and more preferably about 90%, 91%, 92%, 93%, 94%, 95%, 96%, 97%, 98%, 99% or more sequence identity to that particular nucleotide sequence as determined by sequence alignment programs described elsewhere herein using default parameters.

By "variant protein" is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention will continue to possess the desired biological activity of the native protein, that is, anti-pathogenic activity as described herein. Such variants may result from, for example, genetic polymorphism or from human manipulation. Biologically active variants of a native anti-pathogenic protein of the invention will have at least 40%, 50%, 60%, 70%, generally at least 75%, 80%, 85%, preferably about 90% to 95% or more, and more preferably about 90%, 91%, 92%, 93%, 94%, 95%, 96%, 97%, 98%, 99% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

By "stringent conditions" or "stringent hybridization conditions" is intended conditions under which a probe will hybridize to its target sequence to a detectably greater degree than to other sequences (e.g., at least two-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1×to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5×to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m=81.5°$ C.$+16.6$ (log M)$+0.41$ (%GC)$-0.61$ (% form)500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch. (1970) *J. Mol. Biol.* 48:443–453; the search-for-similarity-method of Pearson and Lipman. (1988) *Proc. Natl. Acad. Sci.* 85:2444–2448; the algorithm of Karlin and Altschul (1990) *Proc. Natl. Acad. Sci. USA* 872:264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra A PAM120 weight residue table, a gap length penalty of 12, and a gap penalty of 4 can be used with the ALIGN program when comparing amino acid sequences. The BLAST program of Altschul et al. (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25;3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective program (e.g., BLASTN for nucleotide sequences, BLASTX for proteins) can be used. See www.ncbi.nlm.nib.gov. Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48:443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, 91%, 92%, 93%, 94%, 95%, 96%, 97%, 98%, 99% or more compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, 91%, 92%, 93%, 94%, 95%, 96%, 97%, 98%, more.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90%, 91%, 92%, 93%, 94%, 95%, 96%, 97%, 98%, 99% or more sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

Introduction

Pathogenesis-related protein-5 (PR-5) is one of the ten currently recognized classes of PR proteins. PR-5 (thaumatin-like protein) shares sequence similarity with osmotin, thaumatin, and zeamatin proteins (Hu et al. (1997) *Plant Mol. Biol.* 34:949–959; Ryals et al. (1996) *Plant Cell* 8:1809–1819). PR-5proteins have been characterized from a wide range of plant species representing both dicotyledonous and monocotyledonous plants. Members of this class of proteins have been shown to have antifungal activities against a broad range of fungal pathogens (Hu et al. (1997) *Plant Mol. Biol.* 34:949–959; Ryals et al. (1996) *Plant Cell* 8:1809–1819); Liu et al. (1994) *Proc. Natl. Acad. Sci. USA* 91:1888–1892; Liu et al. (1995) *Plant Mol. Biol.* 29:1015–1026; Zhu et al. (1995) *Plant Physiol.* 108:929–937). In Arabidopsis, the induction of PR-5 is salicylic acid (SA)-dependent. PR5-1, a gene encoding a sunflower homologue of the pathogenesis related protein-5, was isolated and its sequence disclosed in U.S. patent application Ser. No. 09/589,733, entitled "Sunflower Anti-Pathogenic Genes and Proteins and Their Uses," filed Jun. 8, 2000. PR5-1 expression is regulated by oxalate oxidase expression and Sclerotinia infection. A nucleotide sequence encoding a second sunflower pathogenesis-related protein-5

(PR5-2) is disclosed in the present invention (and set forth in SEQ ID NO:1). The PR5-2 nucleotide sequence encodes an amino acid sequence (set forth in SEQ ID NO:2) that shares homology to PR5-1, as well as to other PR proteins. Further provided is the nucleic acid sequence comprising the transcriptional regulatory region of PR5-2 (SEQ ID NO:5). Similar to PR5-1, PR5-2 gene expression is regulated by Sclerotinia infection, and its promoter (SEQ ID NO:5) contains potential pathogen-responsive cis-acting elements, such as an MRE (metal-responsive element). PR5-2 expression is highly induced in root and stem tissues of sunflower plants.

Blight-associated proteins (BAPs) were first discovered in citrus-blight infected trees. BAP is present in the leaves and xylem fluid of roots and stems of trees infected with citrus blight, and the protein has proven useful as a diagnostic marker of this disease (Derrick et al. (1990) Plant Dis. 74:168–170; Derrick et al. (i 992) Proc. Fla: State Hort. Soc. 105:27–28). Northern blot analysis and protein localization assays on tissue isolated from blight-infected trees suggest that the plant transports BAP from the roots and stems to the leaves post-translationally (Ceccardi et al. (1998) Plant Mol. Biol. 38:775–783). The citrus BAP sequence is up to 49% similar and 31% identical to that of expansin, a member of the highly conserved family of proteins associated with the loosening of cell walls during longitudinal growth (McQueen-Mason et al. (1992) Plant Cell 4:1425–1433). An amino acid sequence encoding a sunflower BAP polypeptide (SEQ ID NO:4); a nucleotide sequence encoding the BAP polypeptide (SEQ ID NO:3); and, a nucleotide sequence comprising the transcription regulator region of the BAP sequences (SEQ ID NO:6) are disclosed in the present invention. The BAP cDNA encodes a protein that shares homology (60% identity) with citrus BAP (*Citrus jambhiri*, Accession No. AAD03398).

Nucleotide and Amino Acid Sequences

Compositions and methods for controlling pathogenic agents are provided. In particular, the present invention provides for isolated nucleic acid molecules comprising the nucleotide sequences set forth in SEQ ID NOS:1 and 3, the nucleotide sequences encoding the amino acid sequences set forth in SEQ ID NOS:2 and 4, the nucleotide sequences for the promoters set forth in SEQ ID NOS:5 and 6, the nucleotide sequences encoding the DNA sequences deposited in a bacterial host as Patent Deposit Nos. PTA-563, PTA-561, PTA-564, and PTA-562, or fragments and variants thereof. Further provided are polypeptides having an amino acid sequence set forth in SEQ ID NOS:2 and 4 and those encoded by a nucleic acid molecule described herein, for example those coding sequences set forth in SEQ ID NOS:1 and 3, and fragments and variants thereof.

Methods of the invention utilize these anti-pathogenic compositions to protect plants against fungal pathogens, viruses, nematodes, insects, and the like. Additionally, the compositions can be used in formulations for their antibacterial and antimicrobial activities.

Plasmids containing the BAP and PR5-2 nucleotide sequences and promoter sequences of the invention were deposited with the Patent Depository of the American Type Culture Collection, Manassas, Va., on Aug. 27, 1999, and assigned Patent Deposit Nos. PTA-563 (PR5-2 nucleotide sequences), PTA-561 (PR5-2 promoter sequences), PTA-564 (BAP nucleotide sequences), and PTA-562 (BAP promoter sequences). These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The sequences of the invention find use as anti-pathogenic agents. Thus, the sequences can be used to engineer plants having disease resistance or enhanced disease resistance. In this manner, the sequences can be used alone or in combination with each other and/or with other known disease resistance genes to provide broad-spectrum disease resistance. For example, the PR-5 and BAP gene products may prove to be useful in enhancing disease resistance in transgenic plants also expressing other transgenes. For example, oxalate oxidase-transgenic sunflower plants (herein, "oxox") expressing a wheat oxalate oxidase gene may show higher levels of PR-5 and/or BAP induction in response to Sclerotinia infection (data not shown).

Additionally, the sequences can be used as markers in studying the defense signal pathways and in disease-resistance breeding programs. The sequences can also be used as probes to isolate other signalling components involved in defence/resistance responsiveness and to isolate the corresponding promoter sequences. See, generally, Sambrook et al. (1989) *Molecular Cloning. A Laboratory Manual* (2d ed., Cold Spring Harbor Laboratory Press, Plainview, N.Y.).

Compositions of the invention include the nucleotide sequences for two sunflower nucleic acid sequences designated herein as PR5-2 (set forth in SEQ ID NO:1) and BAP (set forth in SEQ ID NO:3), and the corresponding amino acid sequences encoded thereby (set forth in SEQ ID NOS:2 and 4, respectively). Fragments and variants of these sequences as defined herein are also encompassed by the present invention. These nucleic acid sequences may be assembled into a DNA construct such that the sequence is operably linked to a promoter that drives expression of a coding sequence in a cell of interest. Plants stably transformed with this DNA construct express a protein of the invention. Expression of this protein creates or enhances disease resistance in the transformed plant.

Fragments of the sunflower PR5-2 and BAP sequences disclosed herein are encompassed by the present invention. A fragment of a sunflower PR5-2 or BAP nucleotide sequence may encode a biologically active portion of a sunflower PR5-2 or BAP protein, or it may be a fragment that can be used as a hybridization probe or PCR primer using methods described below. A biologically active portion of a sunflower PR5-2 or BAP protein can be prepared by isolating a portion of one of the sunflower PR5-2 or BAP nucleotide sequences of the invention, expressing the encoded portion of the sunflower PR5-2 or BAP protein (e.g., by recombinant expression in vitro), and assessing the anti-pathogenic activity of the encoded portion of the sunflower PR5-2 or BAP protein. Nucleic acid molecules that are fragments of a sunflower PR5-2 or BAP nucleotide sequence comprise at least 16, 20, 30, 50, 60, 75, 100, 150, 200, 225, 250, 300, 350, 375, 400, 450, 500, 525, or 540 nucleotides, or up to the number of nucleotides present in a full-length sunflower PR5-2 or BAP nucleotide sequence disclosed herein (for example, 910 nucleotides for PR5-2 (SEQ ID NO:1), and 622 nucleotides for BAP (SEQ ID NO:3)).

A fragment of the sunflower PR5-2 or BAP nucleotide sequence that encodes a biologically active portion of the sunflower PR5-2 or BAP protein of the invention will encode at least 15, 25, 30, 50, 75, 100, or 125 contiguous amino acids, or up to the total number of amino acids present in a full-length PR5-2 or BAP protein of the invention (for example 229 amino acid residues for PR5-2 (SEQ ID NO:2), and 130 amino acid residues for BAP (SEQ ID NO:4)). Fragments of a sunflower PR5-2 or BAP nucleotide sequence that are useful as hybridization probes or PCR primers generally need not encode a biologically active portion of a PR5-2 or BAP protein.

In this manner, the present invention encompasses the anti-pathogenic polypeptides as well as fragments thereof. That is, it is recognized that fragments of the proteins may be produced which retain anti-pathogenic protein activity that creates or enhances disease resistance in a plant. These fragments include truncated sequences, as well as N-terminal, C-terminal, internal, and internally deleted amino acid sequences of the proteins.

The polypeptides of the invention may be altered in various ways including amino acid substitutions, deletions, truncations, and insertions to obtain variant proteins that continue to possess the desired anti-pathogenic activity of the native proteins disclosed herein. Methods for such manipulations are generally known in the art. For example, amino acid sequence variants of the proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. *Techniques in Molecular Biology* (MacMillan Publishing Company, New York) and the references cited therein. Guidance as to appropriate amino acid substitutions that do not affect desired biological activity of the native protein may be found in the model of Dayhoff et al. (1978) *Atlas of Protein Sequence and Structure* (Nat'l Biomed. Res. Found., Washington, D.C.), herein incorporated by reference. Conservative substitutions, such as exchanging one amino acid with another having similar properties, may be preferable.

Thus, the nucleotide sequences of the invention include both the naturally occurring sequences as well as mutant forms. Likewise, the proteins of the invention encompass the naturally occurring proteins as well as variations and modified forms thereof. Obviously, the mutations that will be made in the DNA encoding the variant must not place the sequence out of reading frame and preferably will not create complementary regions that could produce secondary mRNA structure. See; EP Patent Application Publication No. 75,444.

The deletions, insertions, and substitutions of the protein sequences encompassed herein are not expected to produce radical changes in the characteristics of the anti-pathogenic proteins. However, when it is difficult to predict the exact effect of the substitution, deletion, or insertion in advance of doing so, one skilled in the art will appreciate that the effect will be evaluated by routine screening assays. That is, the activity of the modified protein sequences can be evaluated by monitoring of the plant defense system. See, for example U.S. Pat. No. 5,614,395, herein incorporated by reference.

Variant nucleotide sequences and proteins also encompass anti-pathogenic nucleotide sequences and proteins derived from a mutagenic and recombinogenic procedure such as DNA shuffling. With such a procedure, one or more different anti-pathogenic gene or protein sequences can be manipulated to create new sequences possessing the desired properties. In this manner, libraries of recombinant polynucleotides are generated from a population of related polynucleotides comprising sequence regions that have substantial sequence identity and can be homologously recombined in vitro or in vivo. For example, using this approach, sequence motifs encoding a domain of interest may be shuffled between the sunflower PR5-2 or BAP nucleotide sequences of the invention and other known anti-pathogenic sequences to obtain new sequences encoding a polypeptide with an improved property of interest, such as a broader spectrum of pathogen resistance. Likewise, sequences corresponding to regulatory motifs, such as specific cis-acting elements within the promoters of the invention may be shuffled creating improved regulatory functions, such as increased pathogen inducibility or an increased expression. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech*. 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The invention also encompasses the 5' regulatory regions of the PR5-2 (shown in FIG. 2) and BAP (shown in FIG. 3) nucleotide sequences disclosed herein. The nucleotide sequences for these native 5' untranslated regions, i.e., promoters, are provided in SEQ ID NOS:5 and 6, respectively. It is recognized that having identified the nucleotide sequences for the promoter regions disclosed herein, it is within the state of the art to isolate and identify further regulatory elements in the 5' untranslated region upstream from the particular promoter regions identified herein. Thus, for example, the promoter regions disclosed herein may further comprise upstream regulatory elements that confer tissue-specific and/or tissue-preferred expression of any heterologous nucleotide sequence operably linked to one of the disclosed promoter sequences. See particularly Australian Patent No. AU-A-77751/94 and U.S. Pat. Nos. 5,466,785 and 5,635,618. Likewise, promoter regions having homology to the promoters of the invention can be isolated by hybridization under stringent conditions, as described elsewhere herein.

Pathogen-responsive cis-acting elements have been identified within these promoter regions, such as an MRE-like element and a ZAP-like element in the PR5-2 promoter, and an MRE element and W-Box in the BAP promoter. These promoters have been identified as having an inducible expression pattern, more specifically a defense-inducible expression pattern. Thus, where gene expression in response to a stimulus is desired, an inducible promoter of the invention is the regulatory element of choice. When using an inducible promoter, expression of the nucleotide sequence is initiated in cells in response to a stimulus are described elsewhere herein.

The 94-bp first intron of the BAP gene (underlined in FIG. 3) can increase BAP promoter activity inducibly or constitutively. This intron sequence can be used to enhance the activity of other promoters by fusing the sequence to other promoter sequences.

The promoter sequences of the invention include both the naturally occurring sequences as well as mutant forms. Such vanent promoter regions can be derived from a mutagenic and recombinogenic procedure such as DNA shuffling. With such a procedure, one or more different promoter sequences can be manipulated to create new sequences possessing the desired properties. In this manner, libraries of recombinant polynucleotides are generated from a population of related sequence polynucleotides comprising sequence regions that have substantial sequence identity and can be homologously recombined in vitro or in vivo. For example, sequences corresponding to regulatory motifs, such as specific cis-acting elements within the promoters of the invention, may be shuffled, creating improved regulatory functions, such as increased pathogen inducibility. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotechnology* 15:436–438; Moore et al. (1997) *J. Mol. Biol.* 272:336–347; Zhang et al. (1997) *Proc. Natl Acad. Sci. USA* 94:4504–4509; Crameri et al. (1998) *Nature* 391:288–291; and U.S. Pat. Nos. 5,605,793 and 5,837,458.

Fragments and variants of the promoter nucleotide sequences disclosed herein are also encompassed by the present invention. A fragment of a sunflower PR5-2 or BAP promoter nucleotide sequence comprises at least 15, 20, 25, 30, 35, 40, 45, 50, 75, 100, 325, 350, 375, 400, 450, 500, 550, 600, 650, 700, 750, 800, 850, 900, 950, 1000, 1050, 1100, 1150, 1200, or 1250 nucleotides, or up to the number of nucleotides present in a full-length promoter nucleotide sequence disclosed herein (for example, 1448 nucleotides and 1291 nucleotides for SEQ ID NOS:5 and 6, respectively). Generally, fragments of a promoter sequence that retain their biological activity (i.e., regulate transcription) comprise at least 30, 35, 40 contiguous nucleotides, preferably at least 50 contiguous nucleotides, more preferably at least 75 contiguous nucleotides, still more preferably at least 100 contiguous nucleotides of the particular promoter nucleotide sequence disclosed herein. Preferred fragment lengths depend upon the objective and will also vary depending upon the particular promoter sequence.

The nucleotides of such fragments will usually comprise the TATA recognition sequence of the particular promoter sequence. Such fragments may be obtained by use of restriction enzymes to cleave the naturally occurring promoter nucleotide sequence disclosed herein, by synthesizing a nucleotide sequence from the naturally occurring sequence of the promoter DNA sequence, or may be obtained through the use of PCR technology. See particularly, Mullis et al. (1987) *Methods Enzymol.* 155:335–350, and Erlich, ed. (1989) *PCR Technology* (Stockton Press, New York). Variants of these promoter fragments, such as those resulting from site-directed mutagenesis, are encompassed by the compositions of the present invention.

The nucleotide sequences of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire BAB or PR5-2 promoter sequences and the BAP or PR5-2 nucleotide sequences of the present invention or to fragments thereof are encompassed by the present invention. Such sequences include sequences that are orthologs of the disclosed sequences. By "ortholdgs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the sunflower PR5-2 or BAP sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire anti-pathogenic coding sequence or portion thereof, or the entire BAP or PR5-2 promoter sequence may be used as a probe capable of specifically hybridizing to corresponding coding sequences, messenger RNAs or genomic DNA. To achieve specific hybridization under a variety of conditions, such probes include sequences that are unique and are preferably at least about 10 nucleotides in length, and most preferably at least about 20 nucleotides in length. Such probes may be used to amplify the anti-pathogenic coding sequences from a chosen organism by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions as qualified elsewhere herein. Isolated sequences that have anti-pathogenic activity and which hybridize under stringent conditions to the PR5-2 and BAP gene sequences disclosed herein, or to fragments thereof, are encompassed by the present invention. Isolated sequences that have promoter activity and which hybridize under stringent conditions to the PR5-2 and BAP promoter sequences are also encompassed by the present invention. Such sequences will be at least 40% to 50% homologous, about 60% to 70% homologous, and even about 75%, 80%, 85%, 90%, 95% to 98% homologous or more with the disclosed sequences. That is, the sequence identity of sequences may range, sharing at least 40% to 50%, about 60% to 70%, and even about 75%, 80%, 85%, 90%, 95% to 98% or more sequence identity.

Expression Cassettes

The nucleotide sequences of the invention are provided in expression cassettes for use in the plant of interest. Expression cassettes may comprise any of the nucleotide sequences of the invention. For example, expression cassettes or DNA constructs of the invention may be provided with a plurality of restriction sites for insertion of an anti-pathogenic sequence to be under the transcriptional regulation of regulatory region(s) of interest. Expression cassettes or DNA constructs may also be provided with a plurality of restriction sites for insertion of a sequence of interest to be placed under the regulatory influence of the promoters of the invention. The expression cassettes may additionally comprise at least one additional gene to be cotransformed into the organism. Alternatively, the additional gene(s) can be provided on multiple expression cassettes. The expression cassette may additionally contain selectable marker genes.

The expression cassettes or DNA constructs of the invention will include in the 5'-to-3' direction of transcription, a transcriptional and translational initiation region, a nucleotide sequence to be expressed, and a transcriptional and translational termination region functional. The transcriptional initiation region, the promoter, may be native or analogous or foreign or heterologous to the plant host. The promoter may also be native or analogous or foreign or heterologous to the nucleotide sequence or coding sequence to be expressed. Additionally, the promoter may be the natural sequence or alternatively a synthetic sequence.

While it may be preferable to express the sequences encoding the anti-pathogenic proteins using heterologous promoters, the native promoter sequences may be used. Such constructs would change expression levels of the anti-pathogenic genes in the plant or plant cell. Thus, the phenotype of the plant or plant cell is altered.

A number of promoters can be used to drive the expression of the coding sequences encoding the anti-pathogenic proteins of the invention. The promoters may be selected based on the desired outcome. For example, the promoters may be selected based on desired timing, localization, and/or level of expression of the anti-pathogenic sequences in a plant. Constitutive, tissue-preferred, pathogen-inducible, and wound-inducible promoters can be used in the practice of the invention.

It may be beneficial to express the disclosed sequences from an inducible promoter, particularly a pathogen-inducible promoter. The inducible promoter will initiate expression of a gene in the presence of a pathogen to prevent infection and disease symptoms. Such promoters include those from other pathogenesis-related proteins (PR proteins), which are induced following infection by a pathogen; e.g., PR proteins, SAR proteins, beta-1, 3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virl.* 4:111–116. See, also the application entitled "Maize PR-1 Genes and Promoters", U.S. application Ser. No. 09/257,583, filed Feb. 25, 1999, herein incorporated by reference.

Of interest are promoters that are expressed locally at or near the site of pathogen infection. See, for example, Marineau et al. (1987) *Plant Mol. Biol.* 1:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Mol. Gen. Genet.* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode,inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189–200).

Additionally, as pathogens find entry into plants through wounds or insect damage, a wound-inducible promoter may be used in the constructions of the invention. Such wound-inducible promoters include potato proteinase inhibitor (pin II) gene (Ryan et al. *Ann. Rev. Phytopath.* 28:425–449; Duan et al. *Nature Biotechnology* 14:494–498); wun1 and wun2, U.S. Pat. No. 5,428,148; win1 and win2 (Stanford et al. *Mol. Gen. Genet.* 215:200–208); systemin (McGurl et al. *Science* 225:1570–1573); WIP1 (Rohmeier et al. *Plant Mol. Biol.* 22:783–792; Eckelkamp et al. *FEBS Letters* 323:73–76); MPI gene (Corderok et al. *Plant J.* 6(2):141–150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al (1991) *Mol. Gen. Genet.* 227:229–237, and U.S. Pat. Nos. 5,814,618 and 5,789,156), herein incorporated by reference.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142.

Tissue-preferred promoters can be used to target anti-pathogenic gene expression within a particular tissue. Tissue-preferred promoters include Yamamoto et al. (1997) *Plant J.* 12(2):255–265; Kawamata et al. (1997) *Plant Cell Physiol.* 38(7):792–803; Hansen et al. (1997) *Mol. Gen. Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol Biol.* 23(6):1129–1138; Matsuoka et al. (1993) *Proc Natl. Acad. Sci. USA* 90(20):9586–9590; and Guevara-Garcia et al. (1993) *Plant J.* 4(3):495–505; Such promoters can be modified, if necessary, for weak expression.

"Seed-preferred" promoters include both "seed-specific" promoters (those promoters active during seed development such as promoters of seed storage proteins) as well as "seed-germinating" promoters (those promoters active during seed germination). See Thompson et al. (1989) BioEssays 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see the copending application entitled "Seed-Preferred Promoters," U.S. application Ser. No. 09/377,648, filed Aug. 19, 1999, herein incorporated by reference) Gama-zein is a preferred endospern-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc.

Leaf-specific promoters are known in the art. See, for example, Yamamoto et al. (1997) Plant J. 12(2):255–265; Kwon et al. (1994) Plant Physiol. 105:357–67; Yamamoto et al. (1994) Plant Cell Physiol. 35(5):773–778; Gotor et al. (1993) Plant J. 3:509–18; Orozco et al. (1993) Plant Mol. Biol. 23(6):1129–1138; and Matsuoka et al. (1993) Proc. Natl. Acad. Sci. USA 90(20):9586–9590.

Root-preferred promoters are known and can be selected from the many available from the literature or isolated de novo from various compatible species. See, for example, Hire et al. (1992) Plant Mol. Biol. 20(2):207–218 (soybean root-specific glutamine synthetase gene); Keller and Baumgartner (1991) Plant Cell 3(10):1051–1061 (root-specific control element in the GRP 1.8 gene of French bean); Sanger et al. (1990) Plant Mol. Biol. 14(3):433–443 (root-specific promoter of the mannopine synthase (MAS) gene of Agrobacterium tumefaciensj; and Miao et al. (1991) Plant Cell 3(1):11–22 (full-length cDNA clone encoding cytosolic glutamine synthetase (GS), which is expressed in roots and root nodules of soybean). See also Bogusz et al. (1990) Plant Cell 2(7):633–641, where two root-specific promoters isolated from hemoglobin genes from the nitrogen-fixing non-legume Parasponia andersonii and the related non-nitrogen-fixing nonlegume Trema tomentosa are described. The promoters of these genes were linked to a β-glucuronidase reporter gene and introduced into both the nonlegume Nicotiana tabacum and the legume Lotus corniculatus, and in both instances root-specific promoter activity was preserved. Leach and Aoyagi (1991) describe their analysis of the promoters of the highly expressed rolC and rolD root-inducing genes of Agrobacterium rhizogenes (see Plant Science (Limerick) 79(1):69–76). They concluded that enhancer and tissue-specific DNA determnninants are dissociated in those promoters. Teeri et al. (1989) used gene fusion to lacZ to show that the Agrobacterium T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see EMBO J. 8(2): 343–350). The TR1' gene, fused to nptII (neomycin phosphotransferase II) showed similar characteristics. Additional root-preferred promoters include the VfENOD-GRP3 gene promoter (Kuster et al. (1995) Plant Mol. Biol. 29(4): 759–772); and rolB promoter (Capana et al. (1994) Plant Mol Biol. 25(4):681–691. See also U.S. Pat. Nos. 5,837,876; 5,750,386; 5,633,363; 5,459,252; 5,401,836; 5,110,732; and 5,023,179.

The termination region may be native with the transcriptional initiation region, may be native with the operably linked DNA sequence of interest, or may be derived from another source. Convenient termination regions are available from the Ti-plasmid of A. tumefaciens, such as the octopine synthase and nopaline synthase termination regions. See also, Guerineau et al. (1991) Mol. Gen. Genet. 262:141–144; Proudfoot (1991) Cell 64:671–674; Sanfacon et al. (1991) Genes Dev. 5:141–1 49; Mogen et al. (1990) Plant Cell 2:1261–1272; Munroe et al. (1990) Gene 91:151–158; Ballas et al. 1989) Nucleic Acids Res. 17:7891–7903; Joshi et al. (1987) Nucleic Acids Res. 15:9627–9639.

Where appropriate, the gene(s) may be optimized for increased expression in the transformed plant. That is, the genes can be synthesized using plant-preferred codons for improved expression. See, for example, Campbell and Gowri (1990) Plant Physiol. 92:1–11 for a discussion of host-preferred codon usage. Methods are available in the art for synthesizing plant-preferred genes. See, for example, U.S. Pat. Nos. 5,380,831 and 5,436,391, and Murray et al. (1989) Nucleic Acids Res. 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences, which may be deleterious to gene expression. The G-C content of the sequence maybe adjusted to levels average for a given cellular host, as calculated by reference to known genes expressed in the host cell. When possible, the sequence is modified to avoid predicted hairpin secondary mRNA structures.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) Curr. Opin. Biotech. 3:506–511; Christopherson et al. (1992) Proc. Nat. Acad. Sci. USA 89:6314–6318; Yao et al. (1992) Cell 71:63–72; Reznikoff (1992) Mol. Microbiol. 6:2419–2422; Barkley et al. (1980) in The Operon, pp. 177–220; Hu et al. (1987) Cell 48:555–566; Brown et al. (1987) Cell 49:603–612; Figge et al. (1988) Cell 52:713–722; Deuschle et al. (1989) Proc. Natl. Acad. Aci. USA 86:5400–5404; Fuerst et al. (1989) Proc. Natl. Acad. Sci. USA 86:2549–2553; Deuschle et al. (1990) Science 248:480–483; Gossen (1993) Ph.D. Thesis, University of Heidelberg; Reines et al. (1993) Proc. Natl. Acad. Sci. USA 90:1917–1921; Labow et al. (1990) Mol. Cell. Biol. 10:3343–3356; Zambretti et al. (1992) Proc. Natl. Acad. Sci. USA 89:3952–3956; Baim et al. (1991) Proc. Natl. Acad. Sci. USA 88:5072–5076; Wyborski et al. (1991) Nucleic Acids Res. 19:4647–4653; Hillenand-Wissman (1989) Topics Mol. Struc. Biol. 10:143–162; Degenkolb et al. (1991) Antimicrob. Agents Chemother. 35:1591–1595; Kleinschnidt et al. (1988) Biochemistry 27:1094–1104; Bonin (1993) Ph.D. Thesis, University of Heidelberg; Gossen et al. (1992) Proc. Natl. Acad. Sci. USA 89:5547–5551; Oliva et al. (1992) Antimicrob. Agents Chemother. 36:913–919; Hlavka et al. (1985) Handbook of Experimental

*Pharmacology*, Vol. 78 ( Springer-Verlag, Berlin); Gill et al. (1988) *Nature* 334:721–724; etc. Such disclosures are herein incorporated by reference. The above list of selectable marker genes is not meant to be limiting. Any selectable marker gene can be used in the present invention.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Gallie et al. (1995) *Gene* 165(2) :233–238), MDMV leader (Maize Dwarf Mosaic Virus) (*Virology* 154:9–20), and human immunoglobulin heavy-chain binding protein (BiP) (Macejak et al. (1991) *Nature* 353:90–94; untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) *Molecular Biology of RNA*, ed. Cech (Liss, N.Y.) pp. 237–256; and maize chlorotic mottle virus leader (MCMV) (Lommel et al. (1991) *Virology* 81:382–385). See also, Della-Cioppa et al. (1987) *Plant Physiology* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions, may be involved.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774–8778; herein incorporated by reference.

Transformation

DNA constructs comprising the BAP or PR5-2 nucleotide sequences, or alternatively, DNA constructs comprising the BAP or PR5-2 promoters operably linked to a nucleotide sequence of interest can be used to transform any host cell (i.e. prokaryotic cells and eukaryotic cells, such as yeast, insect, plant and mammalian cells).

The methods of the invention involve introducing a nucleotide construct into a host cell. By "introducing" is intended presenting to the cell the nucleotide construct in such a manner that the construct gains access to the interior of a cell. The methods of the invention do not depend on a particular method for introducing a nucleotide construct to a host cell, only that the nucleotide construct gains access to the interior of at least one cell of the host (i.e. plant). Methods for introducing nucleotide constructs into host cell are known in the art including, but not limited to, stable transformation methods, transient transformation methods, and virus-mediated methods.

By "stable transformation" is intended that the nucleotide construct introduced into a host cell integrates into the genome of the cell and is capable of being inherited by progeny thereof. By "transient transformation" is intended that a nucleotide construct introduced into a host cell does not integrate into the genome of the cell.

The nucleotide constructs of the invention may be introduced into host cells by contacting cells with a virus or viral nucleic acids. Generally, such methods involve incorporating a nucleotide construct of the invention within a viral DNA or RNA molecule. It is recognized that the PR5-2 or BAP protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

In this manner, genetically modified plants, plant cells, plant tissue, seed, and the like can be obtained. Transformation protocols as well as protocols for introducing nucleotide sequences into plants may vary depending on the type of plant or plant cell, i.e. monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat No. 5,563,055; Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al.

(1988) *Plant Physiol.* 91:440–444 (maize); Fromm et al. (1990) *Biotechnology* 8:833–839 (maize); Hooykaas-Van Slogteren et al. (1984) *Nature (London)* 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. ( 992) *Plant Cell* 4:1495–1505 (electroporation); Li et al. (1993) *Plant Cell Reports* 12:250–255 and Christou and Ford (1995)*Annals of Botany* 75:407–413 (rice); Osjoda et al. (1996) *Nature Biotechnology* 14:745–750 (maize via *Agrobacterium tumefaciens*); all of which are herein incorporated by reference.

The present invention may be used for transformation of any plant species, including, but not limited to, corn (*Zea mays*), Brassica sp. (e.g., *B. napus, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Pnaicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (Lathyrus spp.), and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*),: carnation (*Dianthus caryophyllus*), poinsettia (*Euphorbia puicherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al., *Nature* 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., *Nature* 292:128(1981)). The inclusion of selection markers in DNA vectors transfected in *E coli.* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva et al., *Gene* 22:229–235 (1983); Mosbach, et al., *Nature* 302:543–545 (1983)).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous nucleotide sequences in yeast is well known. Sherman, F., et al., *Methods in Yeast Genetics*, Cold Spring Harbor Laboratory (1982) is a well recognized work describing the various methods available to produce the protein in yeast. Two widely utilized yeasts for production of eukaryotic proteins are *Saccharomyces cerevisiae and Pichia pastoris*. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lists. The monitoring of the purification process can be accomplished by using Western blot techniques or radioimmunoassay of other standard immunoassay techniques.

The sequences of the present invention can also be ligated to various expression vectors for use in transfecting cell cultures of, for instance, mammalian, insect, or plant origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al., *Immunol. Rev.* 89:49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armywormn, moth and Drosophila cell lines such as a Schneider cell line (See, Schneider, *J. Embryol. Exp. Morphol.* 27:353–365 (1987).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc (1997).

Methods for Modulation Expression of the Anti-Pathogenic Sequences

The present invention further provides a method for modulating (i.e., increasing or decreasing) the concentration or composition of the sequences of the present invention in a plant or part thereof. Increasing or decreasing the concentration and/or the composition (i.e., the ratio of the polypeptides of the present invention) in a plant can effect modulation. The method comprises introducing into a plant cell, a recombinant expression cassette comprising a polynucleotide of the present invention as described above to obtain a transformed plant cell, culturing the transformed plant cell under plant cell growing conditions, and inducing or repressing expression of a polynucleotide of the present invention in the plant for a time sufficient to modulate concentration and/or composition in the plant or plant part.

In some embodiments, the content and/or composition of polypeptides of the present invention in a plant may be modulated by altering, in vivo or in vitro, the promoter of a gene to up- or down- regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art and discussed briefly, supra.

In general, concentration or composition is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail below. Induction of expression of a polynucleotide of the present invention can also be controlled by exogenous administration of an effective amount of inducing compound. Inducible promoters and inducing compounds, which activate expression from these promoters, are well known in the art. In preferred embodiments, the polypeptides of the present invention are modulated in monocots, particularly maize.

It is recognized that with these nucleotide sequences, antisense constructions, complementary to at least a portion of the messenger RNA (mRNA) for the BAP or. PR5-2 sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

Pathogens and Pests

The invention is drawn to compositions and methods for inducing resistance in a plant to plant pests. Accordingly, the compositions and methods are also useful in protecting plants against fungal pathogens, viruses, nematodes, insects, and the like.

The invention is drawn to compositions and methods for inducing resistance in a plant to plant pests. Accordingly, the compositions and methods are also useful in protecting plants against fungal pathogens, viruses, nematodes, insects and the like. An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

Assays that measure anti-pathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plants. For example, a plant either expressing an anti-pathogenic polypeptide or having an anti-pathogenic composition applied to its surface shows a decrease in tissue necrosis (i.e., lesion diameter) or a decrease in plant death following pathogen challenge when compared to a control plant that was not exposed to the anti-pathogenic composition. Alternatively, anti-pathogenic activity can be measured by a decrease in pathogen biomass. For example, a plant expressing an anti-pathogenic polypeptide or exposed to an anti-pathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107–15111, herein incorporated by reference.

Furthermore, in vitro anti-pathogenic assays include, for example, the addition of varying concentrations of the anti-pathogenic composition to paper disks and placing the disks on agar containing a suspension of the pathogen of interest. Following incubation, clear inhibition zones develop around the discs that contain an effective concentration of the anti-pathogenic polypeptide (Liu et al. (1994) *Plant Biology* 91:1888–1892, herein incorporated by reference). Additionally, microspectrophotometrical analysis can be used to measure the in vitro antipathogenic properties of a composition (Hu et al. (1997) *Plant Molecular Biology* 34:949–959 and Cammue et al. (1992) *J. Biol. Chem* 267:2228–2233, both of which are herein incorporated by reference).

While the invention is not bound by any particular mechanism of action, the gene products, probably proteins or polypeptides, function to inhibit or prevent plant diseases in a plant. Such gene products may be anti-pathogenic. That is, such gene products may be capable of suppressing, controlling, and/or killing the invading pathogenic organism. It is recognized that the present invention is not dependent upon a particular mechanism of defense. Rather, the genes and methods of the invention work to increase resistance of the plant to pathogens independent of how that resistance is brought about.

The plant defense mechanisms described herein may be used alone or in combination with other proteins or agents to protect against plant diseases and pathogens. Other plant defense proteins include those described in the copending application entitled "Methods for Enhancing Disease Resistance in Plants," U.S. application Ser. No. 09/256,898, filed Feb. 24, 1999, application entitled "Genes for Activation of Plant Pathogen Defense Systems," U.S. application Ser. No. 09/256,158, filed Feb. 24, 1999, and application entitled "Family of Maize PR-1 Genes and Promoters," U.S. application Ser. No. 09/257,583, filed Feb. 25, 1999, all of which are herein incorporated by reference.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma*fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium roftsii, Cercospora kikuchii, Cercospora sojina, Peronospora manshurica, Colletotrichum dematium* (*Colletotichumr truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultimum, Pythium debaryanum*, Tomato spotted wilt virus, Heterodera glycines *Fusarium solani*; Canola: *Albugo candida, Alternaria brassicae, Leptosphaeria maculans, Rhizoctonia solani, Sclerotinia sclerotiorum, Mycosphaerella brassiccola; Pythium ultimum, Peronospora parasitica, Fusarium roseum, Alternaria alternata*; Alfalfa: *Clavibater michiganese* subsp. *insidiosum, Pythium ultimum, Pythiumr irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis*, Fusarium, *Xanthomonas campestris* p.v. *alfalfae, Aphanomyces euteiches, Stemphyliun herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusariurm graminearum, Fusarium avenaceum, Fusarium culmorum, Ustilago tritici, Ascochyta tritici, Cephalosporium gramineum, Collotetrichum graminicola, Erysiphe graminis* fsp. *tritici, Puccinia graminis* f.sp. *tritici, Puccinia recondita* fsp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, High Plains Virus, European wheat striate virus; Sunflower: *Plasmophora halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophomina phaseolina,*

*Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Fusarium mnoniliforme* var. *subglutinans, Erwinia stewartii, Fusarium moniliforme, Gibberella zeae (Fusarium graminearum), Stenocarpella maydi (Diplodia maydis), Pythium irregulare, Pythium debaryanum, Pythium graminicola, Pythium splendens, Pythium ultimum, Pythium aphanidermatum, Aspergillus flavus, Bipolaris maydis O, T (Cochliobolus heterostrophus), Helminthosporium carbonum* I, II & III (*Cochliobolus carbonum*), *Exserohilum turcicum* I, II & III, *Helminthosporium pedicellatum, Physoderma maydis, Phyllosticta mnaydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora,* Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola (Glomerella graminicola), Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Nematodes include parasitic nematodes such as root-knot, cyst, and lesion nematodes, including Heterodera and Globodera spp; particularly *Globodera rostochiensis* and *globodera pailida* (potato cyst nematodes); *Heterodera glycines* (soybean cyst nematode); *Heterodera schachtii* (beet cyst nematode); and *Heterodera avenae* (cereal cyst nematode).

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis,* European corn borer; *Agrotis ipsilon,* black cutworm; *Helicoverpa zea,* corn earworm; *Spodoptera frugiperda,* fall armyworm; *Diatraea grandiosella,* southwestern corn borer; *Elasmopalpus lignosellus,* lesser cornstalk borer; *Diatraea saccharalis,* surgarcane borer; *Diabrotica virgifera,* western corn rootworm; *Diabrotica longicornis barberi,* northern corn rootworm; *Diabrotica undecimpunctata howardi,* southern corn rootworm; Melanotus spp., wireworms; *Cyclocephala borealis,* northern masked chafer (white grub); *Cyclocephala immaculata,* southern masked chafer (white grub); *Popilliajaponica,* Japanese beetle; *Chaetocnema pulicaria,* corn flea beetle; *Sphenophorus maidis,* maize billbug; *Rhopalosiphum maidis,* corn leaf aphid; *Anuraphis maidiradicis,* corn root aphid; *Blissus leucopterus leucopterus,* chinch bug; *Melanoplus femurrubrum,* redlegged grasshopper; *Melanoplus sanguinipes,* migratory grasshopper; *Hylemya platura,* seedcorn maggot; *Agromyza parvicornis,* corn blot leafminer; *Anaphothrips obscrurus,* grass thrips; *Solenopsis milesta,* thief ant; *Tetranychus urticae,* twospotted spider mite; Sorghum: *Chilo partellus,* sorghum borer; *Spodoptera frugiperda,* fall armyworm; *Helicoverpa zea,* corn earworm; *Elasmopalpus lignosellus,* lesser cornstalk borer; *Feltia subterranea,* granulate cutworm; *Phyllophaga crinita,* white grub; Eleodes, Conoderus, and Aeolus spp., wireworms; *Oulema melanopus,* cereal leaf beetle; *Chaetocnema pulicaria,* corn flea beetle; *Sphenophorus maidis,* maize billbug; *Rhopalosiphum maidis*; corn leaf aphid; *Sipha flava,* yellow sugarcane aphid; *Blissus leucopterus leucopterus,* chinch bug; *Contarinia sorghicola,* sorghum midge; *Tetranychuis cinnabarinus,* carmine spider mite; *Tetranychus urticae,* twospotted spider mite; Wheat: *Pseudaletia unipunctata,* army worm; *Spodoptera frugiperda,* fall armyworm; *Elasmopalpus lignosellus,* lesser cornstalk borer; *Agrotis orthogonia,* western cutworm; *Elasmopalpus lignosellus,* lesser cornstalk borer; *Oulema melanopus,* cereal leaf beetle; *Hypera punctata,* clover leaf weevil; *Diabrotica undecimpunctata howardi,* southern corn rootworm; Russian wheat aphid; *Schizaphis graminum,* greenbug; *Macrosiphum avenae,* English grain aphid; *Melanoplus femurrubrum,* redlegged grasshopper; *Melanoplus differentialis,* differential grasshopper; *Melanoplus sanguinipes,* migratory grasshopper; *Mayetiola destructor,* Hessian fly; *Sitodiplosis mosellana,* wheat midge; *Meromyza americana,* wheat stem maggot; *Hylemya coarctata,* wheat bulb fly; *Frankliniella fusca,* tobacco thrips; *Cephus cinctus,* wheat stem sawfly; *Aceria tulipae,* wheat curl mite; Sunflower: *Suleima helianthana,* sunflower bud moth; *Homoeosoma electellum,* sunflower moth; *zygogramma exclamationis,* sunflower beetle; *Bothyrus gibbosus,* carrot beetle; *Neolasioptera murtfeldtiana,* sunflower seed midge; Cotton: *Heliothis virescens,* cotton budworm; *Helicoverpa zea,* cotton bollworm; *Spodoptera exigua,* beet armyworm; *Pectinophora gossypiella,* pink bollworm; *Anthonomus grandis grandis,* boll weevil; *Aphis gossypli,* cotton aphid; *Pseudatomoscelis seriatus,* cotton fleahopper; *Trialeurodes abutilonea,* bandedwinged whitefly; *Lygus lineolaris,* tarnished plant bug; *Melanoplusfemurrubrum,* redlegged grasshopper; *Melanoplus differentialis,* differential grasshopper; *Thrips tabaci,* onion thrips; *Franklinkiella ffusca,* tobacco thrips; *Tetranychus cinnabarinus,* carmine spider mite; *Tetranychus urticae,* twospotted spider mite; Rice: *Diatraea saccharalis,* sugarcane borer; *Spodoptera frugiperda,* fall armyworm; *Helicoverpa zea,* corn earworm; *Colaspis brunnea,* grape colaspis; *Lissorhoptrus oryzophilus,* rice water weevil; *Sitophilus oryzae,* rice weevil; *Nephotettix nigropictus,* rice leafhopper; *Blissus leucopterus leucopterus,* chinch bug; *Acrosternum hilare,* green stink bug; Soybean: *Pseudoplusia includens,* soybean looper; *Anticarsia gemmatalis,* velvetbean caterpillar; *Plat-*

*hypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; Delia ssp., Root maggots.

Molecular Markers

The present invention provides a method of genotyping a plant comprising a polynucleotide of the present invention. The plant may be a monocot, such as maize or sorghum, or alternatively, a dicot, such as sunflower or soybean. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., Clark, ed. (1997) *Plant Molecular Biology: A Laboratory Manual*, Chapter 7 (Springer-Verlag, Berlin). For molecular marker methods, see generally, Paterson (1996) "The DNA Revolution," in *Genome Mapping in Plants*, ed. Paterson (Academic Press/ R. G. Landis Company, Austin, Tex.), pp. 7–21.

The particular method of genotyping in the present invention may employ any umber of molecular marker analytic techniques such as, but not limited to, restriction fragment length polymorphisms (RFLPs). Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5,3, 2, or 1 cM of a gene of the invention.

In the present invention, the nucleic acid probes employed for molecular marker mapping of plant nuclear genomes selectively hybridize, under selective hybridization conditions, to a gene encoding a polynucleotide of the present invention. In some embodiments, the probes are selected from polynucleotides of the present invention. Typically, these probes are cDNA probes or Pst I genomic clones. The length of the probes is discussed in greater detail, supra, but is typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement.

The present invention further provides a method of genotyping comprising the steps of contacting, under stringent hybridization conditions, a sample suspected of comprising a polynucleotide of the present invention with a nucleic acid probe. Generally, the sample is a plant sample, preferably, a sample suspected of comprising a sunflower polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In some embodiments, the nucleic acid probe comprises a polynucleotide of the present invention.

Similarly, the present invention provides a method of diagnosis of pathogen attack of plants. Further, differences in the expression of specific genes between uninfected and infected plants may be determined. For example, differences in the expression of specific genes between uninfected sunflowers and Sclerotinia-infected sunflowers may be determined using gene expression profiling. In gene expression profiling, total RNA or mRNA is analyzed using the gene expression profiling process (GeneCalling®) as described in U.S. Pat. No. 5,871,697, herein incorporated by reference.

Methods of use for the Promoter Sequences

The nucleotide sequences for the BAP and PR5-2 promoters disclosed in the present invention, as well as variants and fragments thereof, are useful in the genetic manipulation of any host (particularly a plant or plant cell) when assembled with a DNA construct such that the promoter sequence is operably linked to a nucleotide sequence encoding a heterologous nucleotide sequence of interest. In this manner, the nucleotide sequences of the promoters of the invention are provided in expression cassettes along with heterologous nucleotide sequences for expression in a host of interest.

The promoter for the BAP and PR5-2 genes may regulate expression of operably linked nucleotide sequences in an inducible manner. That is, expression of the operably linked nucleotide sequences in a plant cell is induced in response to a stimulus. By "stimulus" is intended a chemical, which may be applied externally or may accumulate in response to another external stimulus. A stimulus includes, for example, a pathogen, which may, for example, induce expression as a result of invading a plant cell; wounding or other factor such as environmental stresses, including but not limited to, drought, temperature, and salinity. Hence, the promoter sequences when operably linked to a disease resistance sequence can enhance disease resistance in a transformed plant.

Synthetic hybrid promoter regions are known in the art. Such regions comprise upstream promoter elements of one nucleotide sequence operably linked to the promoter element of another nucleotide sequence. In an embodiment of the invention, heterologous gene expression is controlled by a synthetic hybrid promoter comprising the BAP or PR5-2 promoter sequences of the invention, or a variant or fragment thereof, operably linked to upstream promoter element (s) from a heterologous promoter. Upstream promoter elements that are involved in the plant defense system have been identified and may be used to generate a synthetic promoter. See, for example, Rushton et al. (1998) *Curr. Opin. Plant Biol.* 1:311–315. Alternatively, a synthetic BAP or PR5-2 promoter sequence may comprise duplications of the upstream promoter elements found within the promoter sequence.

It is recognized that the promoter sequence of the invention may be used with its native coding sequences. A DNA construct comprising the BAB or PR5-2 promoter operably linked with its native gene may be used to transform any plant of interest to bring about a desired phenotypic change, such as enhanced disease resistance. Where the promoter and its native gene is naturally occurring within the plant, i.e., in maize, transformation of the plant with these operably linked sequences also results in either a change in phenotype, such as enhanced disease resistance or the insertion of operably linked sequences within a different region of the chromosome thereby altering the plant's genome.

In another embodiment of the invention, expression cassettes will comprise a transcriptional initiation region comprising the promoter sequences disclosed herein, or variants or fragments thereof, operably linked to the heterologous nucleotide sequence. Hence, the promoter nucleotide sequences and methods disclosed herein are useful in regulating expression of any heterologous nucleotide sequence in a host plant in order to vary the phenotype of a plant.

Various changes in phenotype are of interest including modifying the fatty acid composition in a plant, altering the amino acid content of a plant, and the like. Phenotypes that alter the disease resistance of the plant to various abiotic and biotic stresses including pathogens, wounding, and environment stress are of particular interest. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. application Ser. Nos. 08/838,763, filed Apr. 10, 1997; U.S. Pat. No. 08/824,379, filed Mar. 26, 1997; U.S. Pat. No. 08/824,382, filed Mar. 26, 1997; and U.S. Pat. No. 5,703,049; herein incorporated by reference. Another example is lysine and/or sulfur rich seed protein encoded by the soybean 2S albumin described in U.S. application Ser. No. 08/618,911, filed Mar. 20, 1996, and the chymotrypsin inhibitor from barley, described in Williamson et al. (1987) Eur. J. Biochem. 165:99–106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and PCT/US97/20441, filed Oct. 31, 1997, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497–502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,737,514; 5,723,756; 5,593,881; and Geiser et al. (1986) *Gene* 48:109); lectins (Van Damme et al. (1994) *Plant Mol. Biol.* 24:825); and the like.

Genes encoding disease resistance traits include detoxification genes, such as against fumonosin (U.S. application Ser. No. 08/484,815, filed Jun. 7, 1995); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Formulations

Methods are provided for controlling plant pathogens comprising applying an anti-pathogenic amount of a polypeptide or composition of the invention to the environment of the pathogens. The proteins of the invention can be formulated with an acceptable carrier into a pesticidal composition(s) that is, for example, a suspension, a solution, an emulsion, a dusting powder, a dispersible granule, a wettable powder, an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors or other preparations that influence plant growth. One or more agrochemicals including, but not limited to, herbicides, insecticides, fungicides, bacteriocides, nematocides, molluscicides, acaracides, plant growth regulators, harvest aids, and fertilizers, can be combined with carriers, surfactants, or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area or plant to be treated, simultaneously or in succession, with other compounds. In some embodiments, methods of applying an active ingredient of the present invention or an agrochemical composition of the present invention (which contains at least one of the proteins of the present invention) are foliar application, seed coating, and soil application. The number of applications and the rate of application depend on the intensity of infestation by the corresponding pest.

Suitable surface-active agents include, but are not limited to, anionic compounds such as a carboxylate of, for example, a metal; a carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g. polyoxyethylene sorbitar fatty acid esters, block copolymers of ethylene oxide and propylene oxide, acetylenic glycols such as 2, 4, 7, 9-tetraethyl-5-decyn-4, 7-diol, or ethoxylated acetylenic glycols. Examples of a cationic surface-active agent include, for instance, an aliphatic mono-, di-, or polyamine such as an acetate, naphthenate, or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions of the present invention can be in a suitable form for direct application or as concentrate of primary composition, which requires dilution with a suitable quantity of water or other diluent before application. The pesticidal concentration will vary depending upon the nature of the particular formulation, specifically, whether it is a concentrate or to be used directly. The composition contains 1 to 98% of a solid or liquid inert carrier, and 0 to 50%, preferably 0.1 to 50% of a surfactant. These compositions will be administered at the labeled rate for the commercial product, preferably about 0.01 lb–5.0 lb per acre when in dry form and at about 0.01 pts–10 pts per acre when in liquid form.

In a further embodiment, the compositions, as well as the proteins of the present invention can be treated prior to formulation to prolong the activity when applied to the environment of a target pest as long as the pretreatment is not deleterious to the activity. Such treatment can be by chemical and/or physical means as long as the treatment does not deleteriously affect the properties of the composition(s). Examples of chemical reagents include, but are not limited to, halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

The compositions can be applied to the environment of a pest by, for example, spraying, atomizing, dusting, scattering, coating or pouring, introducing into or on the soil, introducing into irrigation water, by seed treatment, or dusting at the time when the pest has begun to appear or before the appearance of pests as a protective measure. It is generally important to obtain good control of pests in the early stages of plant growth, as this is the time when the plant can be most severely damaged. The compositions of the invention can conveniently contain an other insecticide or pesticide if this is thought necessary.

In a further embodiment, formulations of the present invention for use as antimicrobial therapies comprise the anti-pathogenic proteins in a physiologically or pharmaceutically acceptable carrier, such as an aqueous carrier. Thus, formulations for use in the present invention include, but are not limited to, those suitable for parenteral administration, including subcutaneous, intradermal, intramuscular, intravenous and intraarterial administration, as well as topical administration. The formulations may conveniently be presented in unit dosage form and may be prepared by any of the methods well known in the art. Such formulations are described in, for example, *Remington's Pharmaceutical Sciences* (19th ed., Mack Pub. Co., Easton, Pa., 1995).

In the manufacture of a medicament according to the invention, the anti-pathogenic compositions are typically admixed with, inter alia, an acceptable carrier. The carrier must, of course, be acceptable in the sense of being compatible with any other ingredients in the formulation and must not be deleterious or harmful to the patient. The carrier may be a solid or a liquid. One or more anti-pathogenic proteins may be, incorporated in the formulations of the invention, which may be prepared by any of the well-known techniques of pharmacy consisting essentially of admixing the components, optionally including one or more accessory therapeutic ingredients.

Formulations of the present invention may comprise sterile aqueous and non-aqueous injection solutions of the active compound, which preparations are preferably isotonic with the blood of intended recipient and essentially pyrogen free. These preparations may contain anti-oxidants, buffers, bacteriostats, and solutes that render the formulation isotonic with the blood of the intended recipient. Aqueous and non-aqueous sterile suspensions may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline or water for injection immediately prior to use.

In the formulation, the anti-pathogenic protein may be contained within a lipid particle or vesicle, such as a liposome or microcrystal, which may be suitable for parenteral administration. The particles may be of any suitable structure, such as unilamellar or plurilamellar, so long as the targeted cassette is contained therein. Positively charged lipids such as N-[1-(2,3-dioleoyloxi)propyl]-N,N, N-trimethyl-amoniummethylsulfate, or "DOTAP", are particularly preferred for such particles and vesicles. The preparation of such lipid particles is well known. See, e.g., U.S.

Pat. Nos. 4,880,635; 4,906,477; 4,911,928; 4,917,951; 4,920,016; 4,921,757; etc.

The dosage of the anti-pathogenic protein administered will vary with the particular method of administration, the condition of the subject, the weight, age, and sex of the subject, the particular formulation, the route of administration, etc. In general, the protein will be administered in a range of about 1 μg/L to about 10 g/L.

The following examples are offered by way of illustration and not by way of limitation.

EXPERIMENTAL

EXAMPLE 1

Isolation of the Sunflower PR5-2 and BAP cDNA Clones

Plant Material:

Sunflower (Helianthus, SMF3) plants were grown in the greenhouse or growth chamber. Sunflower pathogen *Sclerotinia sclerotiorum* (255M[7]) was maintained on PDA plate at 20° C. in dark.

Preparation of Total RNA:

Sunflower tissues were ground in liquid nitrogen, and total RNA was isolated using the Tri-Reagent Method (Sigma).

Differential Display:

Differential display was carried out according to the method developed by Liang and Pardee (*Science* 257(1992): 967–971) using total RNAs from Sclerotinia-infected and non-infected sunflower leaf tissues. Three petioles per plant (six-week-old) were infected with Sclerotinia mycelia. Leaf tissues were harvested three days after inoculation (see fungal infection method). The potential Sclerotinia-induced cDNA fragments were isolated from the gel and amplified using the primers shown in Table 1.

TABLE 1

Primers used for isolation of cDNA fragments in the differential display assay.

| Gene | SEQ ID NO: | Band ID | Primer | Sequence |
|---|---|---|---|---|
| PR5-2 | 7 | 9998-19-2 | T12MA | AMAA-(A)n |
| | | | AP-4 | 5'-GGTACTCCAC-3' |
| BAP | 8 | 998-7-1 | T12MG | GMAA-(A)n |
| | | | AP-2 | 5'-GACCGCTTGT-3 |

The PCR products were cloned into TA vector (INVITROGEN) and sequenced using ABI 373 Automated DNA sequencer. The gene-specific primers were designed based on the sequences of the cDNA fragments.

Isolation of Full-length cDNA Clone:

Two full-length cDNA clones were isolated using RACE-like PCR-based technology. The sequence information generated from the differential display was used for designing gene-specific primers to amplify the 5' end regions of the target genes. Sclerotinia-infected leaf and oxalate oxidase-transgenic stem cDNA libraries (2:1 ratio) were used as template. To facilitate cloning full-length cDNAs from initial cloned regions, we designed 28-bp vector primers flanking cDNAs on the 5' end of pBS vector and directionally amplified either 5' end of cDNAs of the two genes with their gene-specific primers, respectively (see Table 2).

TABLE 2

Primers used for isolation of full-length cDNA clones; 27164 and 27165 are vector primers.

| Gene | SEQ ID NO: | Code | Orientation | Sequence | cDNA |
|---|---|---|---|---|---|
| PR5-2 | 9 | 32331 | forward | CCATGATGGCAATGGAAGAG | partial, 3'-end |
| | 10 | 27164 | reverse | GCGATTAAGTTGGGTAACGCCAGGGT | |
| | 11 | 27165 | forward | TCCGGCTCGTATGTTGTGTGGAATTG | partial, 5'-end |
| | 12 | 33532 | reverse | AGATTACCCGCACACCTCATTGTCTTGC | |
| | 13 | 35928 | forward | TACAAACATGACTTGTGCCAAAAACCTTC | full-length |
| | 14 | 27164 | reverse | GCGATTAAGTTGGGTAACGCCAGGGT | |
| BAP | 15 | 32496 | forward | TGGTTACAACGCCCTGTAGTCTTG | partial |
| | 16 | 27164 | reverse | GCGATTAAGTTGGGTAACGCCAGGGT | |
| | 17 | 35927 | forward | GTGCCGCACAGATCAAATCTAAGGGTTC | full-length |
| | 18 | 27164 | Reverse | GCGATTAAGTTGGGTAACGCCAGGGT | |

Once the anticipated 5' end of a specific gene with the intact ATG start codon was cloned and sequenced, the full-length cDNA was amplified by a new gene-specific primer containing the upstream of ATG region sequence and vector primer at the 3' end. PCR products were cloned and sequenced by standard methods. PCR reactions were performed in a total volume of 50 μl in 10 mM Tris-HCl, pH 8.3; 1.5 mM MgCl2; 50 mM KCl; 0.1 mM dNTPs; and 0.25 μM of each primer with 0.5 units of advantage cDNA polymerase mix (Clontech).

Northern Blot Assay:

Total RNA (20 μg) was separated in a 1% agarose gel containing formaldehyde (Sambrook et al. (1989) *Molecular Cloning: A Laboratory Manual* (2d ed., Cold Spring Harbor Laboratory Press, Plainview N.Y.), pp. 7.43–7.52). Ethidium bromide was included to verify equal loading of RNA. After transfer onto Hybond N+ membrane, the blots were hybridized with $^{32}$P-labeled PR5-2 or BAP cDNA. Hybridization and washing conditions were performed according to Church and Gilbert (1984) *Proc. Natl Acad. Sci. USA* 81:1991–1995.

Isolation of Defense-inducible Promoters:

Promoter regions of PR5-2 and BAP were isolated from sunflower genomic DNA using Universal GenomeWalker Kit (Clontech) according to the manufacturer's instructions. Restriction digested genomic DNAs were ligated with an adapter to construct pools of genomic DNA fragments for walking by PCR (Siebert et al. (1995) *Nucleic Acids Res.* 23:1087–1088). Gene specific primers were designed for the walking procedure (Table 3).

TABLE 3

Primers for isolation of promoter regions of PR5-2 and BAP.

| Gene | SEQ ID NO: | Biocode | Function | Sequence |
|---|---|---|---|---|
| PR5-2 | 19 | AP1 | primary PCR primer | 5'-GTAATACGACTCACTATAGGGC-3' |
|  | 20 | AP2 | secondary PCR primer | 5'-ACTATAGGGCACGCGTGGT-3' |
|  | 21 | 33532 | gene specific | AGATTACCCGCACACCTCATTGTCTTGC |
| BAP | 19 | AP1 | primary PCR primer | 5'-GTAATACGACTCACTATAGGGC-3' |
|  | 20 | AP2 | secondary PCR primer | 5'-ACTATAGGGCACGCGTGGT-3' |
|  | 22 | 33535 | gene specific | CTAGTTCCACACGCGGCTCTGTTGTTA |

Analysis of Amplified PCR Products:

DNA sequence analysis was carried out with the Sequencer (3.0). Multiple-sequence alignments (Clustal W) of the amino acid sequences were analyzed with Curatool (CuraGen).

Construction of Sunflower cDNA Libraries:

Six-week-old SMF3 sunflower plants were infected with *Sclerotinia sclerotrium* by petiole inoculation with Sclerotinia-infected carrot plugs. Six days after infection, leaf and stem tissues were collected from infected plants for total RNA isolation. Total RNA was also isolated from sunflower oxalate oxidase-transgenic plants (herein, "oxox"; line 610255) expressing a wheat oxalate oxidase gene at the six-week stage. The mRNAs were isolated by mRNA purification kit (BRL) according to the manufacturer's instruction. cDNA libraries were constructed with the ZAP-cDNA synthesis kit into pBluescript phagemid (Stratagene). A cDNA library mixture for PCR cloning was made of Sclerotinia-infected leaf and oxox transgenic stem libraries (2:1 ratio).

Results:

A total of eighteen Sclerotinia highly induced cDNA bands were identified on the displayed sequence gel (Data not shown). Based on a preliminary GenBank database search, two of the bands, 9998-19-2 and 9998-7-1, show sequence homology with pathogenesis-related protein-5 (PR-5) and blight-associated protein (BAP), respectively, at the amino acid sequence level.

The full-length PR5-2 cDNA isolated from the sunflower cDNA library of Sclerotinia-infected sunflower leaf is 910 bp long (set forth in SEQ ID NO:1) with an open reading frame encoding a protein of 229 amino acid residues (set forth in SEQ ID NO:2) having a molecular weight of approximately 24.5 kDa. A GenBank database search revealed that PR5-2 shares a high degree of homology at the amino acid level with other PR5 proteins from plants: the PR5-2 protein shares approximately 74% identity (82% similarity) with tobacco PR5 protein (GenBank Accession No. X12739) and tobacco thaumatin-like protein (GenBank Accession No. X15224); approximately 71% identity (78% similarity) with tobacco thaumatin-like protein (GenBank Accession No. X15223); approximately 70% identity (83% similarity) with Vitus vinifera VVTLI protein (GenBank Accession No. AF003007); and approximately 70% identity (79% similarity) with sunflower PR5-1 protein (U.S. patent application Ser. No. 09/589,733, filed Jun. 8, 2000). Sequence identities and similarities were determined using CLUSTAL W.

The full-length BAP cDNA isolated from the sunflower cDNA library of Sclerotinia-infected sunflower leaf is 622 bp long (set forth in SEQ ID NO:3) with an open reading frame encoding a protein of 130 amino acid residues (set forth in SEQ ID NO:4) having a molecular weight of 13.6 kDa. Sunflower BAP has high similarity (60% identical amino acid residues) with citrus BAP (AAD03398, *Citrus jambhiri*), as determined by CLUSTAL W. However, a GenBank database search revealed that the homology between the sunflower BAP and other reported protein sequences is fairly low, including: U30479, *Oryza sativa* expansin; AF104919 and U30472, *Arabidopsis thaliana*; U03860, cytokinin-induced message in Glycine max; and AC001229, holcus major pollen allergen from Arabidopsis. Further, BAP proteins are considerably shorter than these proteins.

The 5'-flanking sequence of the PR5-2 gene contains a putative TATA-box, a CAAT-box, and two putative pathogen-responsive, MRE-like elements (shown in FIG. 1). Further, nucleotide sequence comparison of the PR5-1 and PR5-2 promoters shows similarity between small identical blocks which include the putative TATA box, indicating that such sequence blocks may constitute conserved sequence motifs, such as cis-acting elements.

The BAP promoter region contains a putative TATA box and two putative pathogen-responsive elements, an MRE-like motif, and a W-box (shown in FIG. 2).

EXAMPLE 2

Induction of Steady-state Level of PR5-2 and BAP Transcripts by Sclerotinia Infection and Chemical Treatment Sunflower plants (SMF3) were planted in 4-inch pots and grown in a greenhouse for the first four weeks. After transfer to a growth chamber, plants were maintained under a 12-hour photoperiod at 22° C. and 80% relative humidity. Six-week-old plants were subjected to fungal infection or chemical treatments as follows.

For fungal infection, plants were inoculated with Sclerotinia-infected carrot plugs. For each plant, three petioles were inoculated and wrapped with 1×2 inch Parafilm®. Plant tissue samples were collected at different time points by immediately freezing the samples in liquid nitrogen and storing them at −80° C. for subsequent analysis.

For chemical treatments, six-week-old plants were sprayed with oxalic acid (OA, 5 mM), hydrogen peroxide ($H_2O_2$, 5 mM), salicyclic acid (SA, 5 mM), and jasmonic acid (JA, 45 μM in 0.1% ethanol). Leaf samples were collected at 0, 6, 12, and 24 hours after application and immediately frozen in liquid nitrogen as above for subsequent analysis.

Total RNA extracts were prepared from Sclerotinia-infected and non-infected sunflower plant tissues and from chemically treated sunflower leaf tissues as previously described in Example 1. Northern blot assays were performed for these total RNA samples as described in Example 1 using $^{32}$P-labeled PR5-2 or BAP cDNA fragments as probes.

Northern blot analysis showed that both PR5-2 and BAP transcripts were highly induced by Sclerotinia infection. Interestingly, induction of PR5-2 occurred in sunflower root, stem, leaf, and petiole tissues, while induction of BAP was strong in leaf and stem but much weaker in root and petiole tissues. Chemical treatments with OA, $H_2O_2$, SA, or JA significantly induced the expression of both PR5-2 and BAP genes.

The Northern Blot analysis was further used to determine the steady state level of PR5-2 and BAP transcripts in Sclerotinia-infected and non-infected sunflower head tissues (data not shown). The PR5-2 transcript is abundant in receptacle, but not in corolla tube and seed tissues. PR5-2 is slightly induced in receptacle by Sclerotinia infection. BAP expression may not be induced by Sclerotinia infection in head tissues, but it is abundant in corolla tube.

EXAMPLE 3

Expression of PR5-2 and BAP in Oxox Transgenic and Non-transgenic Sunflower

Four-, six-, and eight-week-old non-transgenic SMF3 sunflower plants and oxalate oxidase-transgenic sunflower plants (herein, "oxox"; line 610255) expressing a wheat oxalate oxidase gene were harvested and total RNA extracts prepared as described in Example 1.

Northern blot analysis of these total RNA extracts revealed that steady-state levels of both PR5-2 mRNA and BAP mRNA were highly induced in oxox-transgenic leaf tissues starting from about the six-week-old stage (data not shown). Steady-state levels of PR5-2 and BAP transcripts were moderately and highly induced, respectively, in stem tissues of six-week-old oxox transgenic plants.

EXAMPLE 4

Transformation and Regeneration of Transgenic Plants

Immature maize embryos from greenhouse donor plants are bombarded with a plasmid containing the PRi5-2 or BAP gene operably linked to a Rsyn7 promoter and the selectable marker gene PAT (Wohlleben et al. (1988) *Gene* 70:25–37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the PR5-2 or BAP gene operably linked to a Rsyn7 promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each riacrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for expression of PR5-2 or BAP, enhanced disease resistance (i.e., resistance to Sclerotinia infection).

Bombardment and Culture Media

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l Bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-l $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-1 $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H₂O), 0.1 g/l myo-inositol, and 40.0 g/l sucrose (brought to volume with polished D-I H₂O after adjusting pH to 5.6); and 6 g/l bacto-agar (added after bringing to volume with polished D-1 H20), sterilized and cooled to 60° C.

EXAMPLE 5

Sunflower Meristem Tissue Transformation

Sunflower meristem tissues are transformed with an expression cassette containing the PR5-2 or BAP gene operably linked to a ubiquitin promoter as follows (see also European Patent Number EP 0 486233, herein incorporated by reference, and Malone-Schoneberg et al. (1994) *Plant Science* 103:199–207). Mature sunflower seed (*Helianthus annuus L.*) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al.(1990) *Plant Cell Rep.* 9:55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.*, 15:473–497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid (GA₃), pH 5.6, and 8 g/l Phytagar.

The explants are subjected to microprojectile bombardment prior to Agrobacterium treatment (Bidney et al. (1992) *Plant Mol. Biol.* 18:301–313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the PR5-2 or BAP gene operably linked to the ubiquitin promoter is introduced into *Agrobacterium* strain EHA105 via freeze-thawing as described by Holsters et al. (1978) *Mol. Gen. Genet.* 163:181–187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an OD₆₀₀ of about 0.4 to 0.8. The *Agrobacterium* cells are pelleted and resuspended at a final OD₆₀₀ of 0.5 in an inoculation medium comprised of 12.5 mM MES pH 5.7, 1 gm/l NH₄Cl, and 0.3 gm/l MgSO₄.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for PR5–2 or BAP expression and/or activity.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of T₀ plants (parental generation) maturing in the greenhouse are identified by NPTII ELISA and/or by PR5-2 or BAP expression or activity analysis of leaf extracts while trarnsgenic seeds harvested from NPTII-positive T₀ plants are identified by PR5-2 or BAP expression or activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 µm tungsten particles are resuspended in 150 µl absolute ethanol. After sonication, 8 µl of it is dropped on the center of the surface of macrocarrier. Each plate is bombarded twice with 650 psi rupture discs in the first shelf at 26 mm of Hg helium gun vacuum.

The plasmid of interest is introduced into Agrobacterium tumefaciens strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 µg/l kanamycin is resuspended in an inoculation medium (12.5 mM 2-mM 2-(N-morpholino) ethanesulfonic acid, MES, 1 g/l NH₄Cl and 0.3 gil1MgSO₄ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 µg/ml cefotaxime). The plantlets are cultured on the medium for about two weeks under 16-hour day and 26° C. incubation conditions.

Explants (around 2 cm long) from two weeks of culture in 374C medium are screened for PR5-2 or BAP expression and/ or activity using assays known in the art. After positive (i.e., for PR5-2 or BAP expression) explants are identified, those shoots that fail to exhibit PR5-2 or BAP activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for PR5-2 or BAP expression are grafted to Pioneerg hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with Parafilm. After one week of culture on the medium, grafted plants are transferred to soil. In the first two weeks, they are maintained under high humidity conditions to acclimatize to a greenhouse environment.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule comprising a nucleotide sequence selected from the group consisting of:
   a) a nucleotide sequence comprising the sequence set forth in SEQ ID NO: 5; and
   b) a nucleotide sequence comprising the sequence deposited as Patent Deposit No.PTA-561.

2. A DNA construct comprising a nucleotide sequence of claim 1 operably linked to a heterologous nucleotide sequence of interest.

3. A vector comprising the DNA construct of claim 2.

4. A host cell having stably incorporated the DNA construct of claim 2.

5. The host cell of claim 4, wherein said cell is a plant cell.

6. A method for expressing a nucleotide sequence of interest in a cell, said method comprising:
   a) stably incorporating into the cell a DNA construct comprising said nucleotide sequence of interest operably linked to a promoter active in said plant wherein said sequence of interest is heterologous to said promoter and said promoter comprises a nucleotide sequence selected from the group consisting of:
      i) a nucleotide sequence comprising the sequence set forth in SEQ ID NO:5; and
      ii) a nucleotide sequence selected from the group consisting of a sequence deposited as Patent Deposit No. PTA-561; and
   b) culturing said cell under conditions that allows expression of said nucleotide sequence of interest.

7. The method of claim 6, wherein said cell is a plant cell.

8. A plant having stably incorporated into its genome a DNA construct a heterologous nucleotide sequence operably linked to a promoter that is capable of initiating transcription in a plant cell, wherein said promoter comprises the nucleotide sequence of claim 1.

9. The plant of claim 8, wherein said plant is a dicot.

10. The plant of claim 9, wherein said dicot is a sunflower.

11. The plant of claim 10, wherein said plant is a monocot.

12. Transformed seed of the plant of claim 8.

* * * * *

UNITED STATES PATENT AND TRADEMARK OFFICE
CERTIFICATE OF CORRECTION

PATENT NO. : 6,667,427 B1   Page 1 of 1
DATED : December 23, 2003
INVENTOR(S) : Zhongmeng Bao, Jonathan P. Duvick, Xu Hu and Guihua Lu It is certified that error appears in the above-identified patent and that said Letters Patent is hereby corrected as shown below:

<u>Column 60,</u>
Line 27, should read -- DNA construct comprising a heterologous nucleotide sequence operably --
Line 33, should read
11. The plant of claim 8, wherein said plant is a monocot Signed and Sealed this Thirteenth Day of April, 2004

JON W. DUDAS
*Acting Director of the United States Patent and Trademark Office*